US007829322B2

(12) United States Patent
Kodama et al.

(10) Patent No.: US 7,829,322 B2
(45) Date of Patent: Nov. 9, 2010

(54) RECOMBINANT MICROORGANISM COMPRISING INACTIVATION OF THE APRX GENE

(75) Inventors: Takeko Kodama, Nagano (JP); Keiji Endo, Tochigi (JP); Katsuya Ozaki, Tochigi (JP); Junichi Sekiguchi, Nagano (JP)

(73) Assignees: Kao Corporation, Tokyo (JP); Shinshu University, Nagano (JP)

( * ) Notice: Subject to any disclaimer, the term of this patent is extended or adjusted under 35 U.S.C. 154(b) by 552 days.

(21) Appl. No.: 11/722,162

(22) PCT Filed: Dec. 20, 2005

(86) PCT No.: PCT/JP2005/023390

§ 371 (c)(1),
(2), (4) Date: Jun. 19, 2007

(87) PCT Pub. No.: WO2006/068148

PCT Pub. Date: Jun. 29, 2006

(65) Prior Publication Data

US 2009/0081726 A1 Mar. 26, 2009

(30) Foreign Application Priority Data

Dec. 20, 2004 (JP) ............................. 2004-368166

(51) Int. Cl.
*C12N 1/21* (2006.01)
*C12N 15/00* (2006.01)
*C12N 15/57* (2006.01)
*C12N 15/75* (2006.01)
(52) U.S. Cl. ................. 435/252.31; 435/69.1; 536/23.2
(58) Field of Classification Search ........................ None
See application file for complete search history.

(56) References Cited

U.S. PATENT DOCUMENTS

| 5,874,278 | A | 2/1999 | Sloma et al. | |
| 7,494,798 | B2 * | 2/2009 | Berka et al. | ................. 435/209 |
| 7,563,611 | B2 * | 7/2009 | Tohata et al. | ............. 435/252.3 |

(Continued)

FOREIGN PATENT DOCUMENTS

EP          0 130 756 A1      1/1985

(Continued)

OTHER PUBLICATIONS

US-11-722-162-2080-UNIPROT-n2p, Aug. 7, 2009 search results in UniProt_15.5 amino acid sequence database.*

(Continued)

*Primary Examiner*—Manjunath N Rao
*Assistant Examiner*—William W Moore
(74) *Attorney, Agent, or Firm*—Sterne, Kessler, Goldstein & Fox P.L.L.C.

(57) ABSTRACT

A host microorganism capable of increasing productivity of a protein or polypeptide, a recombinant microorganism obtained by introducing a gene encoding a protein or polypeptide into the host microorganism, and a method for producing a protein or polypeptide using the recombinant microorganism are provided.

Also provided is a recombinant microorganism obtained by introducing into a host microorganism a gene encoding a heterologous protein or polypeptide, wherein in said host microorganism the *Bacillus subtilis* aprX gene or a gene corresponding to the aprX gene has been deleted or knocked out, and a method for producing a protein or polypeptide using the recombinant microorganism.

16 Claims, 4 Drawing Sheets

U.S. PATENT DOCUMENTS

| | | | |
|---|---|---|---|
| 7,585,674 B2* | 9/2009 | Sawada et al. | 435/7.1 |
| 2004/0248279 A1* | 12/2004 | Sawada et al. | 435/252.31 |
| 2005/0176097 A1* | 8/2005 | Andersen et al. | 435/69.1 |
| 2008/0009039 A1 | 1/2008 | Tohata et al. | |
| 2008/0014608 A1 | 1/2008 | Endo et al. | |
| 2009/0170154 A1* | 7/2009 | Endo et al. | 435/69.1 |

FOREIGN PATENT DOCUMENTS

| | | |
|---|---|---|
| EP | 0 246 678 A1 | 11/1987 |
| EP | 0 247 647 A1 | 12/1987 |
| EP | 0 369 817 A2 | 5/1990 |
| JP | 03-067582 A | 3/1991 |
| JP | A-04-190793 | 7/1992 |
| JP | 2889095 | 2/1999 |
| JP | A-2000-210081 | 8/2000 |
| JP | A-2001-527401 | 12/2001 |
| JP | 2004-313169 A | 11/2004 |
| WO | WO 98/49328 | 11/1998 |
| WO | WO 2004/033668 A2 | 4/2004 |

OTHER PUBLICATIONS

Chen, M. W., et al., 1993, "Chloramphenicol acetyltransferase, a cytoplasmic protein, is incompatible for export from *Bacillus subtilis*", Journal of Bacteriology, vol. 175, No. 17, pp. 5697-5700.*

Stahl et al., "Replacement of the *Bacillus subtilis* Subtilisin Structrual Gene with an In Vitro-Derived Deletion Mutation," *Journal of Bacteriology* 158:411-418 (1984).

Yang et al., "Cloning of the Neutral Protease Gene of *Bacillus subtilis* and the Use of the Cloned Gene to Create an In Vitro-Derived Deletion Mutation," *Journal of Bacteriology* 160:15-21 (1984).

Guerout-Fleury, AM et al., "Antibiotic-resistance cassettes for *Bacillus subtilis*," Gene 167(1-2): 335-336 (Dec. 1995), Elsevier, New York.

Henrissat B, "A classification of glycosyl hydrolases based on amino acid sequence similarities," Biochem J. 280(Pt 2): 309-16 (Dec. 1991), Portland Press Ltd., UK.

Hoch, JA et al., "Transformation and Transduction in Recombination-defective Mutants of *Bacillus subtilis*," J. Bacteriol. 93: 1925-1937 (Jun. 1967), Am. Soc. Microbiol., Washington, DC.

Honda, K et al., "Extracellular production of human hepatitis B virus preS2 antigen as hybrid proteins with *Bacillus subtilis* alpha-amylases in high-salt-concentration media," Appl Microbiol Biotechnol 40(2-3): 341-347 (Nov. 1993), Springer-Verlag, Berlin, Germany.

Horinouchi, S and B Weisblum, "Nucleotide sequence and functional map of pC194, a plasmid that specifies inducible chloramphenicol resistance," J. Bacteriol 150: 815-825 (May 1982), Am. Soc. Microbiol., Washington, DC.

Horton, RM et al., "Engineering hybrid genes without the use of restriction enzymes: gene splicing by overlap extension," Gene 77: 61-68 (Apr. 1989), Elsevier, New York.

Itaya, M et al., "A neomycin resistance gene cassette selectable in a single copy state in the *Bacillus subtilis* chromosome," Nucleic Acids Res 17: 4410 (Jun. 1989), IRL Press, New York.

Itaya, M. and T Tanaka, "Gene-directed mutagenesis on the chromosome of *Bacillus subtilis* 168," Mol Gen Genet 223(2): 268-72 (Sep. 1990), Springer-Verlag, Berlin, Germany.

Kunst, F., et al., "The complete genome sequence of the gram-positive bacterium *Bacillus subtilis*," Nature 390: 249-56 (Nov. 1997), Macmillan Magazines Ltd, London, UK.

Lipman, DL and WR Pearson, "Rapid and sensitive protein similarity searches," Science 227: 1435-1441 (Mar. 1985), American Association for the Advancement of Science, Washington, DC.

McKenzie T, et al., "The nucleotide sequence of pUB110: some salient features in relation to replication and its regulation," Plasmid 15(2):93-103 (Mar. 1986), Academic Press, Inc., New York.

Vieira, J and J Messing, "Production of single-stranded plasmid DNA," Methods Enzymol 153: 3-11 (Jan. 1987), Academic Press, Inc., New York.

Dialog File No. 351, Derwent World Patents Index, Accession No. 10283277, English abstract and patent family for JP 2000-210081, published Aug. 2, 2000.

Dialog File No. 351, Derwent World Patents Index, Accession No. 6043451, English abstract and patent family for JP 4-190793, published Jul. 9, 1992.

Extended European Search Report for corresponding EPO application No. 05820070.0, mailed Mar. 11, 2009, European Patent Office, Netherlands.

Murashima, K. et al., "Heterologous Production of *Clostridium cellulovorans* engB, Using Protease-Deficient *Bacillus subtilis*, and Preparation of Active Recombinant Cellulosomes," J. Bacteriol., Jan. 2002; 184: 76-81.

Tjalsma, H. et al., "Signal Peptide-Dependent Protein Transport in *Bacillus subtilis*: a Genome-Based Survey of the Secretome," Microbiol. Mol. Biol. Rev., Sep. 2000; 64: 515-547.

Kodama, T. et al., "*Bacillus subtilis* AprX involved in degradation of a heterologous protein during the late stationary growth phase," J Biosci Bioeng, Aug. 2007; 104(2): 135-43.

International Search Report for International Application No. PCT/JP2005/023390, Japanese Patent Office, mailed Apr. 11, 2006.

Patent Abstracts of Japan, abstract of Publication No. JP 2004-313169 A, Recombinant *Bacillus subtilis*, published Nov. 11, 2004, (listed on accompanying PTO/SB/08A as document FP1).

Kawamura et al., "Construction of a *Bacillus subtilis* Double Mutant Deficient in Extracellular Alkaline and Neutral Proteases," *Journal of Bacteriology* 160:442-444 (1984).

Valbuzzi et al., "A novel member of the subtilisin-like protease family from *Bacillus subtilis*," *Micorbiology* 145:3121-3127 (1999).

Wu et al., "Functional Production and Characterization of a Fibrin-Specific Single-Chain Antibody Fragment from *Bacillus subtilis*: Effects of Molecular Chaperones and a Wall-Bound Protease on Antibody Fragment Production," *Applied and Environmental Microbiology* 68:3261-3269 (2002).

* cited by examiner

AprX →

1 : Strain 168   2 : Octuple-deleted strain
3 : aprX-deleted strain   4 : Nonuple-deleted strain ← amylase-PreS2 protein 1 : Strain Kao8   2 : Strain Kao9

RECOMBINANT MICROORGANISM COMPRISING INACTIVATION OF THE APRX GENE

FIELD OF THE INVENTION

The present invention relates to a microorganism used for producing a useful protein or polypeptide and a method for producing the protein or polypeptide.

BACKGROUND OF THE INVENTION

The industrial production using microorganisms is carried out for wide-ranging kinds of useful substances such as amino acids, organic acids, nucleic acid related compounds, antibiotics, carbohydrates, lipids, and proteins as well as alcoholic beverages and foods (e.g., miso (fermented soy paste) and shoyu (soy sauce)). The use of these substances is spreading into the wide field ranging from foods, pharmaceuticals, and commodities (e.g., detergents and cosmetics) to various chemical raw materials.

Improving productivity is one of important challenges for the industrial production of useful substances using microorganisms, and as a procedure therefor there has been performed the breeding of producing microorganisms by genetic techniques such as mutation. A producing microorganism has, particularly recently, come to be more efficiently bred using a recombinant DNA technology or the like owing to the development in microbial genetics and biotechnology, and the development of host microorganisms for gene recombination is under way. By way of example, there has been developed a strain obtained by further improving a microbial strain recognized as safe and good as a host microorganism, such as the *Bacillus subtilis* strain Marburg No. 168.

However, a microorganism originally has a wide variety of gene groups for accommodating itself to environmental changes in nature. Thus, the use thereof has not necessarily been efficient in the industrial production of a protein or the like, which employs limited production media. In particular, the microorganism has many types of proteolytic enzymes for degrading proteins to utilize them as nitrogen and carbon sources. These enzymes degrade a desired protein or the like, which has constituted a great barrier to the production of a foreign protein or the like.

Attempts have been made from long time ago to delete genes of these proteolytic enzymes (protease, peptidase, etc.) to prevent the degradation of desired proteins produced. Particularly for *Bacillus subtilis*, there have been reported, for example, a strain containing deletion of a gene encoding the major extracellular alkaline protease AprE or the neutral protease NprE or deletion of both of these genes (see Non-Patent Documents 1, 2, and 3), strains containing deletion of some of total 8 types of genes for extracellular and cell wall-bound proteases and peptidases (see Table 1 to be described later), and a strain containing deletion of all of the 8 genes for the proteases and peptidases (see Non-Patent Document 4). However, it has been demonstrated by an analysis or like by the present inventors that a proteolytic enzyme activity was still observed in a culture solution even of the microbial strain containing deletion of these 8 types of proteolytic enzyme genes, indicating the induction of degradation of a desired protein. Thus, there has been a need for identification of a causative proteolytic enzyme and a gene thereof.

The *Bacillus subtilis* aprX gene has been presumptively reported to encode AprX, an intracellular serine protease (see Non-Patent Document 5). However, it has not been reported at all that the AprX is present in a medium to degrade useful enzymes or proteins during the secretory production of these enzymes or proteins to reduce the yield thereof.

[Patent Document 1] Japanese Patent No. 288909
[Patent Document 2] Japanese Patent No. 3210315
[Patent Document 3] JP-A-2001-527401
[Non-Patent Document 1] J. Bacteriol., 158: 411 (1984)
[Non-Patent Document 2] J. Bacteriol., 160: 15 (1984)
[Non-Patent Document 3] J. Bacteriol., 160: 442 (1984)
[Non-Patent Document 4] Appl. Environ. Microbiol., 68: 3261 (2002)
[Non-Patent Document 5] Microbiology, 145: 3121-3127 (1999)

DISCLOSURE OF THE INVENTION

The present invention provides a recombinant microorganism obtained by introducing into a host microorganism a gene encoding a heterologous protein or polypeptide,
wherein in said host microorganism the *Bacillus subtilis* aprX gene or a gene corresponding to the aprX gene has been deleted or knocked out.

The present invention also provides a method for producing a protein or polypeptide using the recombinant microorganism.

MODE FOR CARRYING OUT THE INVENTION

Figure 1:
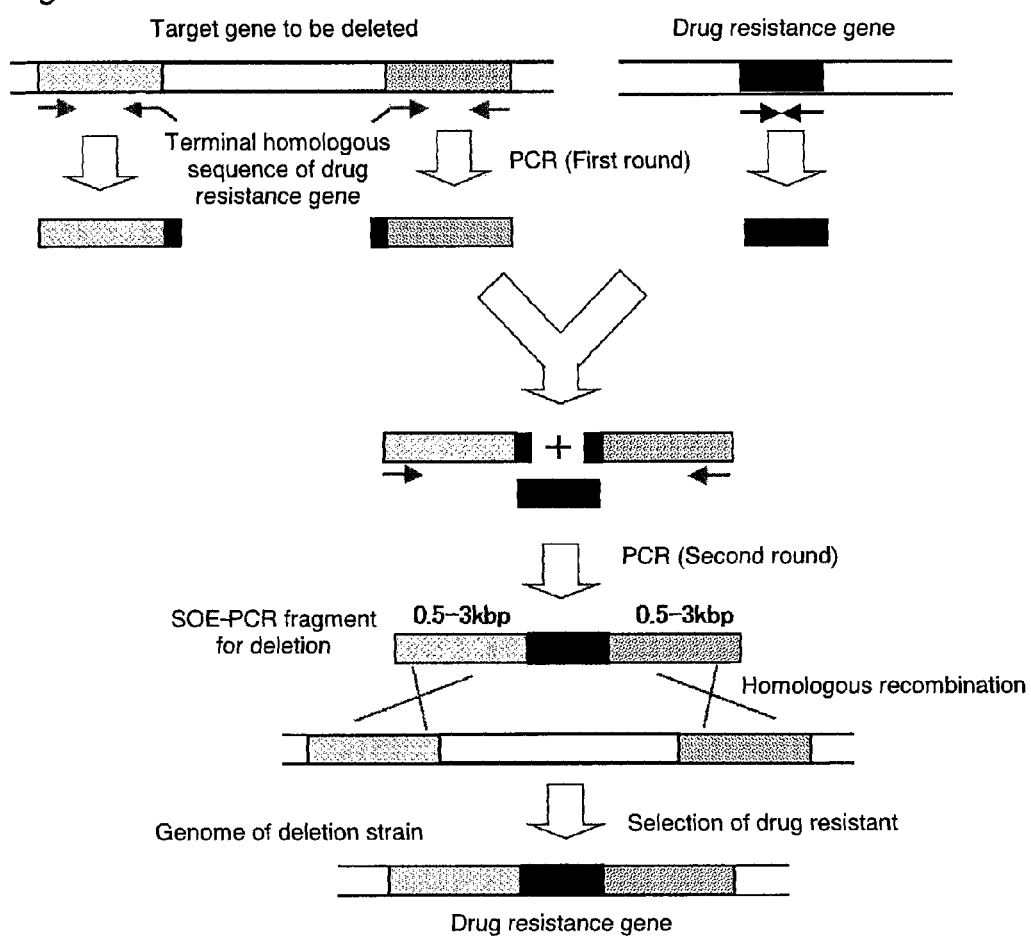
FIG. 1 is a schematic diagram showing the method of preparing a DNA fragment for introducing gene deletion by SOE-PCR and deleting a target gene (replaced by a drug resistance gene) using the DNA fragment.

The present invention provides a recombinant microorganism obtained by preparing a host microorganism enabling the productivity of a protein or polypeptide to be enhanced particularly by the reduction of the production of a proteolytic enzyme and introducing a gene encoding a protein or polypeptide into the host microorganism. The present invention also provides a method for producing a protein or polypeptide using the recombinant microorganism.

The present inventors have searched for a proteolytic enzyme unnecessarily or harmfully acting when a useful protein or polypeptide is produced using a microorganism, and have found that AprX, a putative intracellular serine protease of *Bacillus subtilis*, is present in a medium to degrade useful enzymes or proteins during the secretory production of these enzymes or proteins to reduce the yield thereof. Then, it has been found that a microbial strain containing deletion or inactivation of the *Bacillus subtilis* aprX gene can be used as a host microorganism to greatly prevent the degradation of a useful foreign enzyme or protein, enabling efficient production of the enzyme or protein.

Use of the recombinant microorganism of the present invention can prevent the degradation of a desired protein or polypeptide and enables the protein or polypeptide to be efficiently produced on a large scale.

According to the present invention, the identity of amino acid and base sequences is calculated using the Lipman-Pearson method (Science, 227: 1435 (1985)). More specifically, the identity is calculated by analysis using the search homology program of the genetic information processing software Genetyx-Win (from Software Development) and setting Unit Size to Compare (ktup)=2.

The host microorganism for constructing the microorganism of the invention (hereinafter also referred to as "parent microorganism") desirably has the *Bacillus subtilis* aprX gene (Gene Number: BG12567 in Nature, 390: 249-256 (1997) and Japan Functional Analysis Network for Bacillus subtilis (BSORF DB, bacillus.genome.ad.jp, updated: Jun. 17, 2003) or a gene corresponding to the aprX gene, and these genes may also be wild-type or mutated-type ones. Specific examples thereof include bacteria of the genus *Bacillus* such as *Bacillus subtilis*, those of the genus *Clostridium*, and yeasts; among these, bacteria of the genus *Bacillus* are preferable. In addition, *Bacillus subtilis* is preferable in that the whole genome information thereof has been revealed and a genetic or genomic engineering technique has been established thereon and in that the bacterium is capable of extracellular secretory production of proteins.

The gene to be deleted or inactivated in the present invention is the aprX gene, which has been presumptively reported to encode the intracellular serine protease AprX (Microbiology, 145: 3121 (1999); Gene Number: BG12567 (Nature, 390: 249-256 (1997); JAFAN: Japan Functional Analysis Network for Bacillus subtilis (BSORF DB, bacillus.genome.ad.jp, updated: Jun. 17, 2003), or a gene corresponding to the aprX gene.

Examples of the gene corresponding to the aprX gene include a gene derived from a microorganism other than *Bacillus subtilis*, preferably from a bacterium of the genus *Bacillus*, having the same function as the aprX gene of *Bacillus subtilis* or having a nucleotide sequence identity of 70% or more, preferably 80% or more, more preferably 90% or more, still more preferably 95% or more, yet still more preferably 98% or more with the aprX gene. Specific examples thereof include the BH1930 gene (aprX gene) of *Bacillus halodurans* and the OB2375 gene of *Oceanobacillus iheyensis*.

The object of the present invention can be also achieved by inactivating a target gene using a method involving, for example, inserting into the above-described gene a different DNA fragment or subjecting to mutation the transcription/translation initiation control region of the gene; however, a method involving physically deleting the target gene is more preferable.

As genes to be deleted or inactivated, one or more genes encoding other proteases known to be extracellularly secreted or to be binding to the cell surface may be also deleted in combination with the aprX gene or a gene corresponding to the aprX gene. In addition, the microorganism of the present invention can also be constructed by the combination of deletion or inactivation of genes for intracellular proteases or other genes, which is expected to have a greater effect on the enhancement of productivity. In Table 1 are described genes encoding proteases extracellularly secreted or binding to the cell surface other than the *Bacillus subtilis* aprX gene or a gene corresponding to the aprX gene, which are each deleted or inactivated in combination with the aprX gene or a gene corresponding to the aprX gene to expect the effect. Here, in addition to the aprX gene, preferably deleted or inactivated is at least one gene selected from the aprE, nprB, nprE, bpr, vpr, mpr, epr and wprA genes or from 9 types of genes corresponding to these genes. More preferably deleted or inactivated are the aprE and nprE genes encoding the major extracellular alkaline protease AprE and the neutral protease NprE, respectively, as well as the aprX gene, or 3 types of genes corresponding to these genes. Particularly preferably deleted or inactivated are all of the aprE, nprB, nprE, bpr, vpr, mpr, epr and wprA genes as well as the aprX gene, or 9 types of genes corresponding to these genes.

TABLE 1

| Gene name | Gene number | Gene function and others |
|---|---|---|
| aprE | BG10190 | Serine alkaline protease (subtilisin E) |
| nprB | BG10691 | Extracellular neutral protease B |
| nprE | BG10448 | Extracellular neutral metal protease |
| mpr | BG10690 | Extracellular metal protease |
| bpr | BG10233 | Bacillopeptidase F |
| epr | BG10561 | Minor extracellular serine protease |
| vpr | BG10591 | Minor extracellular serine protease |
| wprA | BG11846 | Cell wall-bound protease precursor (CWBP23, CWBP52) |

Desired genes may be deleted or inactivated not only by a method involving deleting or inactivating, by design, the aprX gene or a gene corresponding to the aprX gene and further a protease gene shown in Table 1 but also by a method involving subjecting these genes to random deletion or inactivating mutation, followed by performing evaluation of protein productivity and gene analysis using suitable means.

For deletion or inactivation of a target gene, a method using homologous recombination may be employed, for example. Specifically, by a method such as PCR, there is constructed a target gene into which an inactivating mutation is introduced by base substitution, base insertion or the like, a linear DNA fragment containing the outside regions of a target gene but not a target gene, or the like. The construct can be then taken up in the cell of a parent microorganism to cause homologous recombination with two crossovers in the two outside regions of a target gene mutation site in the genome of the parent microorganism or in the two outside regions of a target gene therein to replace the target gene on the genome with the target gene-deleted or -inactivated DNA fragment. Alternatively, a DNA fragment containing a portion of a target gene can be cloned in a suitable plasmid, followed by taking up the resultant cyclic recombinant plasmid in the cell of a parent microorganism to interrupt a target gene on the genome of the parent microorganism by homologous recombination in the partial region of the target gene for inactivation of the target gene on the genome.

There have already been reported several methods for deleting or inactivating a target gene by homologous recombination (Mol. Gen. Genet., 223: 268 (1990) and so on), which can be used particularly when *Bacillus subtilis* is employed as a parent microorganism for constructing the microorganism of the present invention. These methods can be each repeated to provide the microorganism of the present invention.

The random gene deletion or inactivation can also be carried out, for example, by a method involving inducing homologous recombination similar to that described in the above-described method using randomly cloned DNA fragments or by a method involving irradiating a parent microorganism with γ-rays or the like.

A deletion method by double crossing-over is more specifically described below which uses a DNA fragment for introduction of deletion prepared by the SOE (splicing by overlap extension)-PCR method (Gene, 77: 61 (1989)). However, the gene-deletion method according to the present invention is not intended to be limited to the following.

The DNA fragment for introduction of deletion used in this method is a fragment in which a drug resistance marker gene fragment is inserted between an about 0.2 to 3 kb fragment adjacent upstream of a gene to be deleted and an about 0.2 to 3 kb fragment adjacent downstream thereof. Three fragments, i.e., the fragments upstream and downstream of the gene to be deleted and the drug resistance marker gene fragment, are first prepared by a first round of PCR. Here, primers used have been designed so that a 10- to 30-base-pair upstream sequence of the drug resistance marker gene is added to the downstream end of the above upstream fragment, while a 10- to 30-base-pair downstream sequence of the marker gene is added to the upstream end of the above downstream fragment (FIG. 1).

The three types of PCR fragments prepared in the first round are used as templates to perform a second round of PCR employing a primer for the upstream side of the upstream fragment and a primer for the downstream side of the downstream fragment to produce the addition of the drug resistance marker gene sequence to the downstream end of the upstream fragment and the upstream end of the downstream fragment. Here, the annealing to the drug resistance marker gene fragment occurs, and PCR amplification can provide a DNA fragment in which the drug resistance marker gene is inserted between the upstream and downstream fragments (FIG. 1).

When a spectinomycin resistance gene is used as the drug resistance marker gene, SOE-PCR is performed using, for example, a set of primers as shown in Table 2, suitable template DNAs, a common enzyme kit for PCR such as Pyrobest DNA Polymerase (from Takara Shuzo), and the like under typical conditions as described in texts (PCR Protocols. Current Methods and Applications, Edited by B. A. White, Humana Press, pp 251 (1993), Gene, 77: 61 (1989) and so on) to provide a DNA fragment for introducing a deletion of each gene.

When the DNA fragment for introducing deletion thus obtained is introduced into cells by a competent cell transformation method (J. Bacteriol. 93: 1925 (1967)) or the like, intracellular genetic recombination occurs in homologous regions upstream and downstream of a gene to be deleted, having identity thereto; the resultant cells in which the target gene has been replaced with the drug resistance gene can be isolated by selection with the drug resistance marker (FIG. 1). Specifically, when the DNA fragment for introducing deletion prepared using a set of primers as shown in Table 2 has been introduced, a colony may be isolated which grows on an agar medium containing spectinomycin, followed by confirming, for example, by a PCR method using the genome as a template, that the desired gene has been replaced with the spectinomycin resistance gene.

As the method for deleting a protease gene containing the aprX gene or a gene corresponding to the aprX gene according to the present invention, there may be also used a 2-stage single-crossover method employing a plasmid for introducing deletion into which a DNA fragment for introducing deletion prepared by the SOE-PCR method is inserted. The method is described below.

Figure 2:
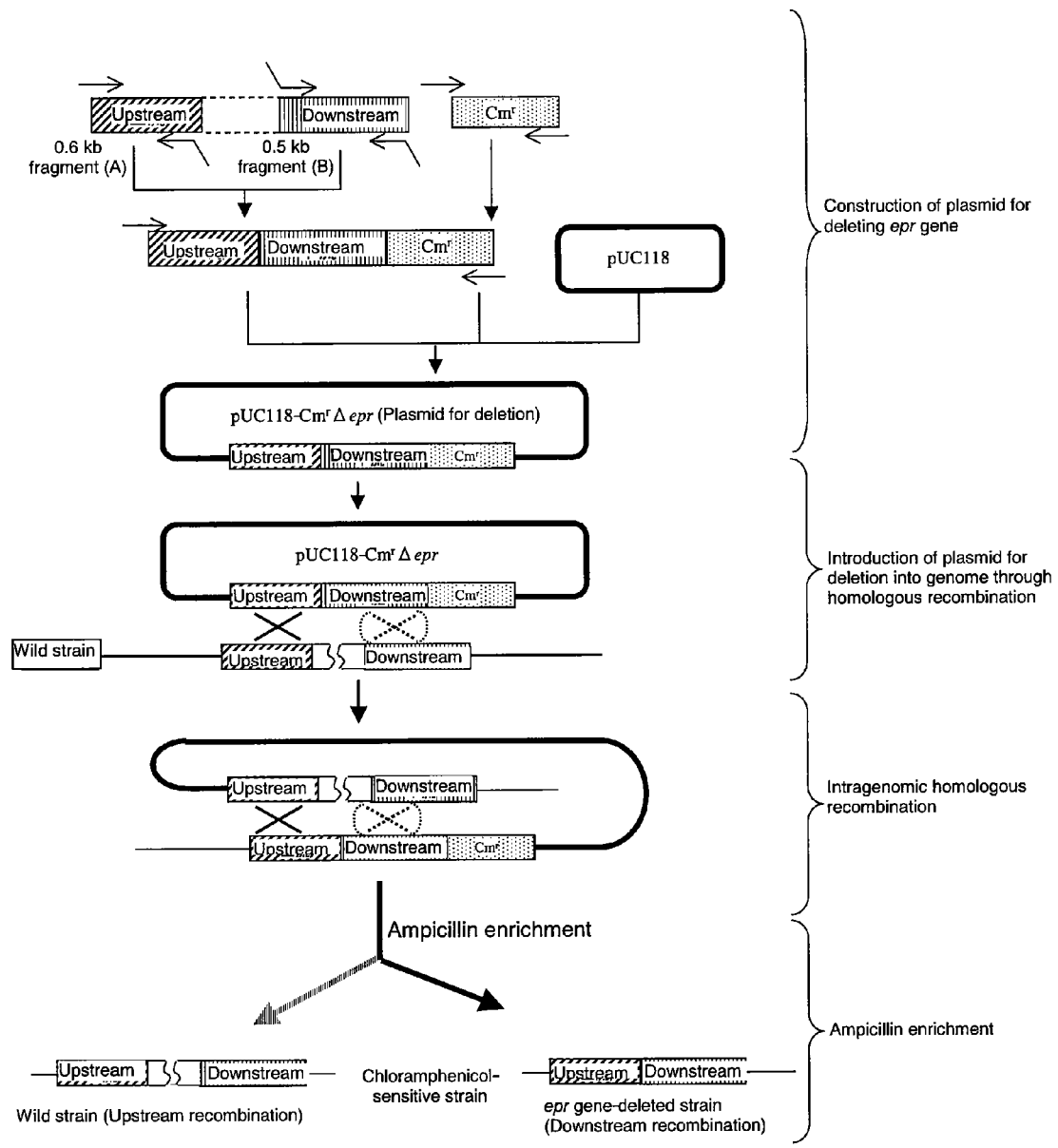
FIG. 2 is a schematic diagram showing the method of preparing a DNA fragment for gene deletion by SOE-PCR, constructing a plasmid for introducing gene deletion using the DNA fragment, and deleting a target gene employing the plasmid.

The DNA fragment for introduction of deletion used in this method is a DNA fragment in which an about 0.2 to 3 kb fragment adjacent to upstream of a gene to be deleted is linked to an about 0.2 to 3 kb fragment adjacent to downstream thereof. A DNA fragment may be also used in which a drug resistance marker gene fragment such as a chloramphenicol resistance gene is linked downstream or upstream of the above DNA fragment. Three fragments, i.e., the fragments upstream and downstream of the gene to be deleted and, if necessary, the drug resistance marker gene fragment, are first prepared by a first round of PCR. Here, primers to each of which a sequence of terminal 10 to 30 base pairs of the DNA fragment to be attached is added is used. By way of example, when the upstream and downstream fragments and the drug resistance marker gene fragment are linked together, primers which have been designed so that a 10- to 30-base-pair upstream sequence of the downstream fragment is added to the downstream end of the upstream fragment and a 10- to 30-base-pair upstream sequence of the marker gene fragment to the downstream end of the downstream fragment may be used (FIG. 2).

The PCR fragments prepared in the first round can be then mixed and used as templates to perform a second round of PCR employing a pair of primers capable of forming the most upstream side and the most downstream side in a desired linked fragment to prepare the desired DNA fragment for introducing deletion. By way of specific example, when the upstream and downstream fragments and the drug resistance marker gene fragment are linked together, a second round of PCR is performed using a primer for the upstream side of the upstream fragment and a primer for the downstream side of the drug resistance marker gene fragment. Here, annealing occurs between the downstream fragment added to the downstream end of the upstream fragment and a sequence homologous thereto and between the drug resistance marker gene fragment added to the downstream end of the downstream fragment and a sequence homologous thereto, followed by PCR amplification to provide a DNA fragment for introducing deletion in which the upstream and downstream fragments and the drug resistance marker gene fragment are linked together (FIG. 2).

The DNA fragment for introducing deletion obtained by the above method or the like is further inserted, using a conventional restriction enzyme and DNA ligase, into a plasmid DNA not amplified in host cells or a readily removable plasmid DNA such as a temperature sensitive plasmid to construct a plasmid for introducing deletion. Non-limiting examples of the plasmid DNA not amplified in the host cell include pUC18, pUC118, and pBR322, for example, when *Bacillus subtilis* is used as a host.

Subsequently, host cells are transformed with the plasmid for introducing deletion using a competent cell transformation method (J. Bacteriol. 93: 1925 (1967)) or the like to provide a transformant in which the plasmid is fused into the host cell genome DNA, through single crossover-mediated homologous recombination between the upstream or downstream fragment inserted into the plasmid and a homologous region on the genome (FIG. 2). The transformant may be selected using as an indication drug resistance due to a marker gene such as a chloramphenicol resistance gene in the plasmid for introducing deletion.

On the genome of the transformant thus obtained, there exists, in duplicate, the sequences of regions upstream and downstream of a gene to be deleted such as the aprX gene or a gene corresponding to the aprX gene derived from the host genome and the plasmid for introducing deletion. Intragenomic homologous recombination is caused between the upstream or downstream regions in an area different from that in which homologous recombination has been made in acquiring the transformant to produce the deletion of a target gene to be deleted such as the aprX gene and a gene corresponding to the aprX gene as well as a region derived from the plasmid for introducing deletion, containing the drug resistance marker gene (FIG. 2). Methods for causing the intragenomic homologous recombination include, for example, a method involving inducing competence (J. Bacteriol. 93: 1925 (1967)); however, the homologous recombination spontaneously occurs even simply during culture in a conventional medium. A strain in which the intragenomic homologous recombination has been caused as intended undergoes the simultaneous deletion of the drug resistance marker gene to lose the ability to resist the drug; thus, the strain can be selected from strains having become drug-sensitive. A genomic DNA may be extracted from the strain, followed by identifying the deletion of the desired gene using a PCR method or the like.

In selecting the desired deletion strain, it is difficult to directly select a strain having changed from a drug-resistant strain into a drug-sensitive one because intragenomic homologous recombination probably occurs at a slightly low frequency on the order of $10^{-4}$. Accordingly, to obtain the desired deletion strain efficiently, it is desirable to perform devices such as increasing the abundance ratio of the drug-sensitive strain. Methods for enriching the drug-sensitive strain include, for example, an enrichment method based on the fact that penicillin antibiotics such as ampicillin bactericidally act on proliferating cells, but do not act on non-proliferating cells (Methods in Molecular Genetics, Cold Spring Harbor Labs (1970)). For enrichment using ampicillin or the like, it is necessary to use a resistance gene to a drug bacteriostatically acting on host cells, such as chloramphenicol, as a drug resistance marker gene of a plasmid for introducing deletion. A resistant strain holding the drug resistance gene can proliferate in a suitable medium containing an appropriate amount of such a drug having a bacteriostatic action, while a sensitive strain containing deletion of the drug resistance gene neither proliferates nor dies out. When the culture is performed by adding a suitable concentration of a penicillin antibiotic such as ampicillin under such conditions, the resistant strain attempting to proliferate dies out, while the sensitive strain does not undergo the action of ampicillin or the like. This results in an increased abundance ratio of the sensitive strain. A culture solution which has been subjected to such enrichment operation can be smeared and cultured on a suitable agar medium, followed by identifying the presence of resistance to the marker drug in colonies which have appeared, using a replica method or the like to select the sensitive strain efficiently.

A gene encoding a desired protein or polypeptide can be introduced into the host microorganism mutant strain, constructed by a method as described above, in which at least one protease gene containing the *Bacillus subtilis* aprX gene or a gene corresponding thereto is deleted or inactivated to provide a recombinant microorganism of the present invention.

Examples of the desired protein or polypeptide produced using the microorganism of the present invention include various industrial enzymes such as those used in detergents, foods, fiber, feeds, chemical goods, medicine, and diagnosis, and proteins or polypeptides such as bioactive factors. Examples of industrial enzymes by function include oxidoreductases, transferases, hydrolases, lyases, isomerases, and ligases/synthetases; preferred examples thereof include genes for hydrolases such as cellulases, α-amylases, and proteases. Specific examples thereof include cellulases belonging to the family 5 in Classification of Polysaccharide Hydrolases (Biochem. J., 280: 309 (1991)); there are exemplified, among others, by cellulases derived from microorganisms, particularly from bacteria of the genus *Bacillus*. More specific examples thereof include alkaline cellulase derived from bacteria of the genus *Bacillus*, containing the amino acid sequence represented by SEQ ID NO: 2 or 4, and an alkaline cellulase having the amino acid sequence in which one or several amino acid residues are deleted, replaced, or added; there is further exemplified by a cellulase containing an amino acid sequence having a sequence identity of 70%, preferably 80%, more preferably 90% or more, still more preferably 95% or more, yet still more preferably 98% or more with the above amino acid sequence (SEQ ID NO: 2 or 4).

Examples of the α-amylase include microorganism-derived α-amylases; particularly preferred are liquefying type amylases derived from bacteria of the genus *Bacillus*. More specific examples thereof include alkaline amylase derived from bacteria of the genus *Bacillus*, containing the amino acid sequence represented by SEQ ID NO: 61, and an amylase containing an amino acid sequence having a sequence identity of 70%, preferably 80%, more preferably 90% or more, still more preferably 95% or more, yet still more preferably 98% or more with the amino acid sequence. In this respect, the identity of amino acid sequences is calculated by the Lipman-Pearson method (Science, 227: 1435, (1985)). Specific examples of the protease include serine or metal proteases derived from microorganisms, particularly from bacteria of the genus *Bacillus*.

In addition, examples of the protein produced by the present invention include bioactive proteins or enzymes derived from higher organisms such as human. Preferred examples thereof include interferon-α, interferon-β, growth hormone, and salivary amylase. Some of domains or the like constituting a bioactive protein can also be expressed; examples thereof include the antigen recognition domain PreS2 of human anti-type C hepatitis virus antibody.

Upstream of a desired protein or polypeptide gene, there is preferably properly linked at least one region selected from control regions involved in the transcription and translation of the gene and the secretion of a product thereof: a transcription initiation control region containing a promoter and a transcription initiation point; a translation initiation control region containing a ribosome binding site and an initiating codon; and a secretion signal peptide-encoding region. More preferably, the three regions containing the transcription initiation control region, the translation initiation control region, and the secretion signal peptide-encoding region are linked. Still more preferably, to the desired protein or polypeptide, there are linked a secretion signal peptide-encoding region derived from a cellulase gene of bacteria of the genus *Bacillus* and transcription initiation control and translation initiation control regions located between 0.6 and 1 kb upstream of the cellulase gene. By way of example, to the structural gene of the desired protein or polypeptide, there are preferably properly linked the transcription initiation control region, translation initiation control region and secretion signal peptide-encoding region of a cellulase gene derived from bacteria of the genus *Bacillus* as described in JP-A-2000-210081 and JP-A-04-190793 and so on, that is, the strain KSM-S237 (deposited Apr. 14, 2003 under Accession Number FERM BP-7875 in International Patent Organism Depositary, National Institute of Advanced Industrial Science and Technology located at Tsukuba Central 6, 1-1-1 Higashi, Tsukuba, Ibaraki, Japan (postal code: 305-8566)) and the strain KSM-64 (deposited Apr. 14, 2003 under Accession Number FERM BP-2886 in International Patent Organism Depositary, National Institute of Advanced Industrial Science and Technology located at Tsukuba Central 6, 1-1-1 Higashi, Tsukuba, Ibaraki, Japan (postal code: 305-8566)). More specifically, to the structural gene of the desired protein or polypeptide, there are preferably properly linked the base sequence of the base no. 1 to 659 in the base sequence represented by SEQ ID NO: 1, the base sequence of the base no. 1 to 696 in the cellulase gene comprising the base sequence represented by SEQ ID NO: 3, a DNA fragment comprising a base sequence having a sequence identity of 70% or more, preferably 80% or more, more preferably 90% or more, still more preferably 95% or more, yet still more preferably 98% or more with the base sequence (SEQ ID NO: 1 or 3), or a DNA fragment containing any one of the above base sequences, portions of which are deleted. Here, the DNA fragment containing the above base sequence, a portion of which is deleted, means a DNA fragment containing the above base sequence, a portion of which is deleted, but holding functions involved in the transcription and translation of the gene and the secretion of a product thereof.

The DNA fragment containing a gene encoding a desired protein or polypeptide can be linked to a suitable plasmid vector, followed by causing the cell of a host microorganism to take up the resultant recombinant plasmid by a common transformation method to provide a recombinant microorganism of the present invention. A DNA fragment in which the above DNA fragment is linked to a suitable region of the host microorganism's genome, homologous thereto, can be also incorporated directly into the host microorganism's genome to provide a recombinant microorganism of the present invention.

The production of a desired protein or polypeptide using a recombinant microorganism of the present invention may be performed by inoculating the microbial strain into a medium containing utilizable carbon and nitrogen sources and other essential components, performing the culture using a conventional microbial culture method, and, after the end of culture, collecting and purifying the protein or polypeptide. The components and composition of the medium is not particularly limited; a medium containing maltose or maltooligosaccharide is preferably used as a carbon source, which provides better results.

According to the above-described methods, a host microorganism mutant strain can be prepared containing deletion or inactivation of any one of the *Bacillus subtilis* genes shown in Table 1, or at least one gene selected from genes corresponding to the these genes, and a recombinant microorganism can be constructed using the mutant strain. The use of the recombinant microorganism enables a useful protein or polypeptide to be produced efficiently.

EXAMPLES

The Examples below specifically describe the following: Construction of a microorganism containing deletion of total 9 types of protease genes including the *Bacillus subtilis* aprX gene (BG12567), and production of cellulase or the antigen recognition domain PreS2 of human anti-type B hepatitis virus antibody using the microorganism as a host; Construction of a microorganism containing deletion of total 3 types of protease genes including the aprX gene (BG12567) in addition to the aprE gene (BG10190) and nprE gene (BG10448) encoding two major extracellular proteases, and production of the antigen recognition domain PreS2 of human anti-type B hepatitis virus antibody using the microorganism as a host.

TABLE 2

| Primer | Sequence | SEQ ID NO: |
|---|---|---|
| eprfw1 | CTCCGGCAGAAAGGGCAT | 5 |
| eprUPr | CGTTCAGCCGTACAACAAGTTTGCAAGACATG | 6 |
| eprDNf | AACTTGTTGTACGGCTGAACGCCGTCAAACC | 7 |
| eprrv-repU | CTGATCTCGACTTCGTTCAGACGGGTCGTACAATGGCTG | 8 |
| repUfw | GAACGAAGTCGAGATCAG | 9 |
| Cmrv1 | GCTGTAATATAAAACCTTCT | 10 |
| eprfw2 | CGACACCATAGCTTTCTG | 11 |
| Cmrv2 | AACTAACGGGGCAGGTTA | 12 |
| repUr-CmU | AGAATCAATCCCATGGTCTCACTTTTCCACTTTTTGTCTTG | 13 |
| CmUf repU | GTGAGACCATGGGATTGATTCTAATGAAGAAAGCAGACAAG | 14 |
| wprAfw1 | GGGTAATTTATCTGATAGGG | 15 |
| wprAUPr | CTTTTGCTTCCCACAACCGAGCTGAATTTTCTG | 16 |
| wprADNf | CTCGGTTGTGGGAAGCAAAAGTTGTTGTTGAAAA | 17 |
| wprArv-repU | CTGATCTCGACTTCGTTCATCCTCATTGAAGACGGCATC | 18 |
| wprAfw2 | GGAACATATATGACACACCT | 19 |
| mprfw1 | TGTTTGGTGTTGAGCTGTT | 20 |

TABLE 2-continued

| Primer | Sequence | SEQ ID NO: |
|---|---|---|
| mprUPr | TTCGTGTGAATCCATTGTTTTCTGAATCTTGGAA | 21 |
| mprDNf | GAAAACAATGGATTCACACGAACGGAGGATCGT | 22 |
| mprrv-repU | CTGATCTCGACTTCGTTCCTCGTAAGAAAAAATACCTATTTC | 23 |
| mprfw2 | CCTTGCGAAAGATAGGGTA | 24 |
| nprBfw1 | TTTTTAGCAGTGGTGCTC | 25 |
| nprBUPr | CATACGCCTTCAGTAATAGAGATGTCTTGGTC | 26 |
| nprBDNf | CTCTATTACTGAAGGCGTATGAGGCTGTCGGC | 27 |
| nprBrv-repU | CTGATCTCGACTTCGTTCTTCCAAATGCGCTTCATTAGGA | 28 |
| nprBfw2 | CTTTTGAGCCCGTTCCTC | 29 |
| bprfw1 | TGAGATTGTGGTGACAGTG | 30 |
| bprUPr | TTAAGTTTTCCGCTGATGAGTCTGTTTTTCGTT | 31 |
| bprDNf | GACTCATCAGCGGAAAACTTAATATGAACACAGAA | 32 |
| bprrv-repU | CTGATCTCGACTTCGTTCGTAATCATGACACCGTTTTGAAC | 33 |
| bprfw2 | ATTGCAACCGGCTTTATCG | 34 |
| nprEfw1 | TTTTGAAGACGTTCGGCGA | 35 |
| nprEUPr | ATTGTCTGTTGCTGAAGCAGCCTGGAATGCTGTT | 36 |
| nprEDNf | CAGGCTGCTTCAGCAACAGACAATTTCTTACCTA | 37 |
| nprErv-repU | CTGATCTCGACTTCGTTCCCTCTCTTAAGTAAGCGCTG | 38 |
| nprEfw2 | TCTCTTTGTTGAAAAACGATA | 39 |
| vprfw1 | AAAAACATCCCTCCGCTTC | 40 |
| vprUPr | TCTTCGGTCAATACAAGCAGAAAGCGAATGAT | 41 |
| vprDNf | TCTGCTTGTATTGACCGAAGAACCTTTCACTG | 42 |
| vprrv-repU | CTGATCTCGACTTCGTTCTGCTCGGCTCATCTGGAGAAA | 43 |
| vprfw2 | TTTTTGGCAGGCAGCCTT | 44 |
| aprEfw1 | CTGTTTATTATGGGCCACGAA | 45 |
| aprEUPr | GATCAGCTTGGGGTTAATCAACGTACAAGCAG | 46 |
| aprEDNf | TGATTAACCCCAAGCTGATCCACAATTTTTTGC | 47 |
| aprErv-repu | CTGATCTCGACTTCGTTCTGATTTTCCAAACGAGCTTTC | 48 |
| aprEfw2 | ATGGGCCATTATGTCATGAAG | 49 |
| aprX + 5F | TTGGGTACTCTATGGTAC | 50 |
| aprX + 563R | CACTGGCCGTCGTTTTACCCATGACCATTATCATCG | 51 |
| aprX + 775F | CATGGTCATAGCTGTTTCCTTATGAGCATGTCGCTCG | 52 |
| aprX + 1320R | GGGAACGGAATTTTCTGC | 53 |
| PB-M13-20 | GTAAAACGACGGCCAGTG | 54 |
| PB-M13Rev | GGAAACAGCTATGACCATG | 55 |
| aprXfw1 | TTCTTTATCATCCTCATGG | 56 |
| aprXUPr | TACAAATGGTGAACGCAGAAAATTCCGTTC | 57 |

TABLE 2-continued

| Primer | Sequence | SEQ ID NO: |
|---|---|---|
| aprXDNf | TTTTCTGCGTTCACCATTTGTACCATAGAG | 58 |
| aprXrv-repu | CTGATCTCGACTTCGTTCTAACAACCTCACTTGGCAA | 59 |
| aprXfw2 | ATAGATCGGCGCCTGAAA | 60 |

TABLE 3

| For deleting epr gene | For deleting wprA gene | For deleting mpr gene | For deleting nprB gene | For deleting bpr gene | For Deleting nprE gene | For deleting vpr gene | For deleting aprE gene | For deleting aprX gene |
|---|---|---|---|---|---|---|---|---|
| eprfw1 | wprAfw1 | mprfw1 | nprBfw1 | bprfw1 | nprEfw1 | vprfw1 | aprEfw1 | aprXfw1 |
| eprUPr | wprAUPr | mprUPr | nprBUPr | bprUPr | nprEUPr | vprUPr | aprEUPr | aprXUPr |
| eprDNf | wprADNf | mprDNf | nprBDNf | bprDNf | nprEDNf | vprDNf | aprEDNf | aprXDNf |
| eprrv-repU | wprArv-repU | mprrv-repU | nprBrv-repU | bprrv-repU | nprErv-repU | vprrv-repU | aprErv-repu | aprXrv-repu |
| eprfw2 | wprAfw2 | mprfw2 | nprBfw2 | bprfw2 | nprEfw2 | vprfw2 | aprEfw2 | aprXfw2 |
| Cmrv2 | Cmrv2 | Cmrv2 | Cmrv2 | Cmrv2 | Cmrv2 | Cmrv2 | Cmrv2 | Cmrv2 |
| repufw | repUfw | repUfw | repUfw | repUfw | repUfw | repUfw | repUfw | repUfw |
| Cmrv1 | Cmrv1 | Cmrv1 | Cmrv1 | Cmrv1 | Cmrv1 | Cmrv1 | Cmrv1 | Cmrv1 |
| repUr-CmU | repUr-CmU | repUr-CmU | repUr-CmU | repUr-CmU | repUr-CmU | repUr-CmU | repUr-CmU | repUr-CmU |
| CmUf-repU | CmUf-repU | CmUf-repU | CmUf-repU | CmUf-repU | CmUf-repU | CmUf-repU | CmUf-repU | CmUf-repU |

Example 1

Construction of a Plasmid for Deleting the epr Gene

Using as a template the genome DNA extracted from the *Bacillus subtilis* strain 168, a 0.6 kb fragment (A) adjacent upstream of the epr gene on the genome and a 0.5 kb fragment (B) adjacent downstream thereof were prepared employing the primer sets of eprfw1 and eprUpr, and eprDNf and eprrv-rep, respectively, as shown in Table 2. A 1.2 kb fragment (C) was also separately prepared in which the promoter region of the repU gene (Nucleic Acids Res. 17: 4410 (1989)) derived from the plasmid pUB110 (Plasmid 15: 93 (1986)) was linked upstream of a chloramphenicol resistance gene derived from the plasmid pC194 (J. Bacteriol. 150 (2): 815 (1982)). The resultant three fragments (A), (B), and (C) were then mixed and used as templates to perform SOE-PCR employing the primers eprfw2 and Cmrv2 in Table 2 to link the three fragments so as to be in the order (A)-(B)-(C) to provide a 2.2 kb DNA fragment (see FIG. 2). The ends of this DNA fragment were blunted, 5'-phosphorylated, and inserted into the SmaI restriction enzyme site of the plasmid pUC118 (Methods Enzymol. 153: 3 (1987)) to construct plasmid pUC118-CmrΔepr for deleting the epr gene. In this respect, the above 1.2 kb fragment (C) was prepared by mixing and using as templates a 0.4 kb fragment (D) containing the repU gene promoter region and a 0.8 kb fragment (E) containing a chloramphenicol resistance gene, followed by performing SOE-PCR employing the primers repUfw and Cmrv1 as shown in Table 2. The fragment (D) was prepared using the primer set of repUfw and repUr-Cm (Table 2) and, as a template, the plasmid pUB110. The fragment (E) was prepared using the primer set of CmUf-rep and Cmrv1 (Table 2) and, as a template, the plasmid pC194.

Example 2

Construction of an epr Gene-Deleted Strain Using a Plasmid for Deletion

The plasmid pUC118-CmrΔepr for deleting the epr gene constructed in Example 1 was introduced into the *Bacillus subtilis* strain 168 by a competent cell transformation method (J. Bacteriol. 93: 1925 (1967)) and fused to the genome DNA by single crossover-mediated homologous recombination between corresponding regions upstream or downstream of the epr gene, followed by obtaining the transformant strain using chloramphenicol resistance as an indication. The resultant transformant strain was inoculated into an LB medium, cultured at 37° C. for 2 hours, and then again subjected to competence induction to induce intragenomic homologous recombination between the regions upstream or downstream of the epr genes present in duplicate on the genome. As shown in FIG. 2, when homologous recombination occurs in a region different from that into which the plasmid has been introduced, the omission of the plasmid-derived chloramphenicol resistance gene and pUC118 vector region involves the deletion of the epr gene. To increase the abundance ratio of a strain having become sensitive to chloramphenicol, an ampicillin enrichment operation was then carried out in the following manner. After inducing competent cells, the culture solution was inoculated into 1 mL of an LB medium containing a final concentration of 5 ppm of chloramphenicol and a final concentration of 100 ppm of ampicillin sodium so as to provide a turbidity (OD600) of 0.003 at 600 nm. The culture solution was cultured at 37° C. for 5 hours, to which 10 μL of a 10,000 ppm ampicillin sodium aqueous solution was then added, followed by culture for further 3 hours. After the end of culture, the cells were subjected to centrifugal washing with a 2% sodium chloride aqueous solution and then suspended in 1 mL of a 2% sodium chloride aqueous solution, followed by smearing 100 μL of the suspension on an LB agar medium. The smear was incubated at 37° C. for about 15 hours; from strains having grown, a strain was then selected which had become sensitive to chloramphenicol with the omission of the plasmid region. Using the genome DNA of the selected strain as a template, PCR was performed employing the primers eprfw2 and eprrv-rep as shown in Table 2 to identify the deletion of the epr gene to provide an epr gene-deleted strain.

Example 3

Construction of a Protease Genes Octuple-Deleted Strain

With respect to the epr gene-deleted strain, the deletion of the wprA gene was performed as the next deletion in the same way as that for the epr gene deletion. Specifically, pUC118-CmrΔwprA, a plasmid for deleting the wprA gene, was constructed as described in Example 1, followed by the introduction of the constructed plasmid into the genome DNA and the subsequent deletion of the wprA gene through intragenomic homologous recombination to provide an epr gene-wprA gene double-deleted strain. The same operation was subsequently repeated to delete the mpr, nprB, bpr, nprE, vpr and aprE genes sequentially. Finally, a protease genes octuple-deleted strain containing deletion of the 8 types of genes was constructed and designated as strain Kao8. The sequences of the primers used for the deletions are shown in Table 2; the correspondence is given in Table 3 between each primer and the primer used for deleting the epr gene shown in Example 1.

SEQ ID NO:5 is the oligonucleotide as PCR sense primer designed from the nucleotide sequence of the 5'-flanking region of the *Bacillus subtilis* gene, epr;

SEQ ID NO:6 is the oligonucleotide as PCR anti-sense primer designed from the nucleotide sequence of the *Bacillus subtilis* gene, epr;

SEQ ID NO:7 is the oligonucleotide as PCR sense primer designed from the nucleotide sequence of the *Bacillus subtilis* gene, epr;

SEQ ID NO:8 is the PCR anti-sense primer which consists of a 3'-portion designed from the nucleotide sequence of the 3'-flanking region of the Bacillus subtilis gene, epr and a 5'-portion designed from the nucleotide sequence of plasmid pUB110;

SEQ ID NO:9 is the oligonucleotide as PCR sense primer designed from the nucleotide sequence of plasmid pUB110;

SEQ ID NO:10 is the PCR anti-sense primer designed from the nucleotide sequence of plasmid pC194;

SEQ ID NO:11 is the oligonucleotide as PCR sense primer designed from the nucleotide sequence of the 5'-flanking region of the *Bacillus subtilis* gene, epr;

SEQ ID NO:12 is the oligonucleotide as PCR anti-sense primer designed from the nucleotide sequence of plasmid pC194;

SEQ ID NO:13 is the PCR anti-sense primer which consists of a 3'-portion designed from the nucleotide sequence of plasmid pUB110 and a 5'-portion designed from the nucleotide sequence of plasmid pC194;

SEQ ID NO:14 is the PCR sense primer which consists of a 3'-portion designed from the nucleotide sequence of plasmid pC194 and a 5'-portion designed from the nucleotide sequence of plasmid pUB110;

SEQ ID NO:15 is the oligonucleotide as PCR sense primer designed from the nucleotide sequence of the 5'-flanking region of the *Bacillus subtilis* gene, wprA;

SEQ ID NO:16 is the oligonucleotide as PCR anti-sense primer designed from the nucleotide sequence of the 5'-flanking region of the *Bacillus subtilis* gene, wprA;

SEQ ID NO:17 is the oligonucleotide as PCR sense primer designed from the nucleotide sequence of the *Bacillus subtilis* gene, wprA;

SEQ ID NO:18 is the PCR anti-sense primer which consists of a 3'-portion designed from the nucleotide sequence of the 3'-flanking region of the Bacillus subtilis gene, wprA and a 5'-portion designed from the nucleotide sequence of plasmid pUB110;

SEQ ID NO:19 is the oligonucleotide as PCR sense primer designed from the nucleotide sequence of the 5'-flanking region of the *Bacillus subtilis* gene, wprA;

SEQ ID NO:20 is the oligonucleotide as PCR sense primer designed from the nucleotide sequence of the 5'-flanking region of the *Bacillus subtilis* gene, mpr;

SEQ ID NO:21 is the oligonucleotide as PCR anti-sense primer designed from the nucleotide sequence of the *Bacillus subtilis* gene, mpr;

SEQ ID NO:22 is the oligonucleotide as PCR sense primer designed from the nucleotide sequence of the *Bacillus subtilis* gene, mpr;

SEQ ID NO:23 is the PCR anti-sense primer which consists of a 3'-portion designed from the nucleotide sequence of the 3'-flanking region of the Bacillus subtilis gene, mpr and a 5'-portion designed from the nucleotide sequence of plasmid pUB110;

SEQ ID NO:24 is the oligonucleotide as PCR sense primer designed from the nucleotide sequence of the 5'-flanking region of the *Bacillus subtilis* gene, mpr;

SEQ ID NO:25 is the oligonucleotide as PCR sense primer designed from the nucleotide sequence of the 5'-flanking region of the *Bacillus subtilis* gene, nprB;

SEQ ID NO:26 is the oligonucleotide as PCR anti-sense primer designed from the nucleotide sequence of the *Bacillus subtilis* gene, nprB;

SEQ ID NO:27 is the oligonucleotide as PCR sense primer designed from the nucleotide sequence of the *Bacillus subtilis* gene, nprB;

SEQ ID NO:28 is the PCR anti-sense primer which consists of a 3'-portion designed from the nucleotide sequence of the 3'-flanking region of the Bacillus subtilis gene, nprB and a 5'-portion designed from the nucleotide sequence of plasmid pUB110;

SEQ ID NO:29 is the oligonucleotide as PCR sense primer designed from the nucleotide sequence of the 5'-flanking region of the *Bacillus subtilis* gene, nprB;

SEQ ID NO:30 is the oligonucleotide as PCR sense primer designed from the nucleotide sequence of the 5'-flanking region of the *Bacillus subtilis* gene, bpr;

SEQ ID NO:31 is the oligonucleotide as PCR anti-sense primer designed from the nucleotide sequence of the *Bacillus subtilis* gene, bpr;

SEQ ID NO:32 is the oligonucleotide as PCR sense primer designed from the nucleotide sequence of the *Bacillus subtilis* gene, bpr;

SEQ ID NO:33 is the PCR anti-sense primer which consists of a 3'-portion designed from the nucleotide sequence of the 3'-flanking region of the Bacillus subtilis gene, bpr and a 5'-portion designed from the nucleotide sequence of plasmid pUB110;

SEQ ID NO:34 is the oligonucleotide as PCR sense primer designed from the nucleotide sequence of the 5'-flanking region of the *Bacillus subtilis* gene, bpr;

SEQ ID NO:35 is the oligonucleotide as PCR sense primer designed from the nucleotide sequence of the 5'-flanking region of the Bacillus subtilis gene, nprE;

SEQ ID NO:36 is the oligonucleotide as PCR anti-sense primer designed from the nucleotide sequence of the Bacillus subtilis gene, nprE;

SEQ ID NO:37 is the oligonucleotide as PCR sense primer designed from the nucleotide sequence of the Bacillus subtilis gene, nprE;

SEQ ID NO:38 is the PCR anti-sense primer which consists of a 3'-portion designed from the nucleotide sequence of the 3'-flanking region of the Bacillus subtilis gene, nprE and a 5'-portion designed from the nucleotide sequence of plasmid pUB110;

SEQ ID NO:39 is the oligonucleotide as PCR sense primer designed from the nucleotide sequence of the 5'-flanking region of the Bacillus subtilis gene, nprE;

SEQ ID NO:40 is the oligonucleotide as PCR sense primer designed from the nucleotide sequence of the 5'-flanking region of the Bacillus subtilis gene, vpr;

SEQ ID NO:41 is the oligonucleotide as PCR anti-sense primer designed from the nucleotide sequence of the 5'-flanking region of the Bacillus subtilis gene, vpr;

SEQ ID NO:42 is the oligonucleotide as PCR sense primer designed from the nucleotide sequence of the Bacillus subtilis gene, vpr;

SEQ ID NO:43 is the oligonucleotide as PCR anti-sense primer which consists of a 3'-portion designed from the nucleotide sequence of the 3'-flanking region of the Bacillus subtilis gene, vpr and a 5'-portion designed from the nucleotide sequence of plasmid pUB110;

SEQ ID NO:44 is the oligonucleotide as PCR sense primer designed from the nucleotide sequence of the 5'-flanking region of the Bacillus subtilis gene, vpr;

SEQ ID NO:45 is the oligonucleotide as PCR sense primer designed from the nucleotide sequence of the 5'-flanking region of the Bacillus subtilis gene, aprE;

SEQ ID NO:46 is the oligonucleotide as PCR anti-sense primer designed from the nucleotide sequence of the Bacillus subtilis gene, aprE;

SEQ ID NO:47 is the oligonucleotide as PCR sense primer designed from the nucleotide sequence of the Bacillus subtilis gene, aprE;

SEQ ID NO:48 is the PCR anti-sense primer which consists of a 3'-portion designed from the nucleotide sequence of the 3'-flanking region of the Bacillus subtilis gene, aprE and a 5'-portion designed from the nucleotide sequence of plasmid pUB110;

SEQ ID NO:49 is the oligonucleotide as PCR sense primer designed from the nucleotide sequence of the 5'-flanking region of the Bacillus subtilis gene, aprE;

SEQ ID NO:50 is the oligonucleotide as PCR sense primer designed from the nucleotide sequence of the Bacillus subtilis gene, aprX;

SEQ ID NO:51 is the PCR anti-sense primer which consists of a 3'-portion designed from the nucleotide sequence of the Bacillus subtilis gene, aprX and a 5'portion designed from the nucleotide sequence of plasmid pBluescript II SK(+);

SEQ ID NO:52 is the oligonucleotide as PCR anti-sense primer designed from the nucleotide sequence of the Bacillus subtilis gene, aprX;

SEQ ID NO:53 is the PCR anti-sense primer; its 3'-portion was designed from the nucleotide sequence of the Bacillus subtilis gene, aprX and its 5'-portion was designed from the nucleotide sequence of the plasmid pBluescript II SK(+);

SEQ ID NO:54 is the oligonucleotide as PCR sense primer designed from the nucleotide sequence of plasmid pBluescript II SK(+);

SEQ ID NO:55 is the oligonucleotide as PCR anti-sense primer designed from the nucleotide sequence of plasmid pBluescript II SK(+);

SEQ ID NO:56 is the oligonucleotide as PCR sense primer designed from the nucleotide sequence of the 5'-flanking region of the Bacillus subtilis gene, aprX;

SEQ ID NO:57 is the oligonucleotide as PCR anti-sense primer designed from the nucleotide sequence of the Bacillus subtilis gene, aprX;

SEQ ID NO:58 is the oligonucleotide as PCR sense primer designed from the nucleotide sequence of the Bacillus subtilis gene, aprX;

SEQ ID NO:59 is the oligonucleotide as PCR anti-sense primer which consists of a 3'-portion designed from the nucleotide sequence of the 3'-flanking region of the Bacillus subtilis gene, aprX and a 5'-portion designed from the nucleotide sequence of plasmid pUB110;

SEQ ID NO:60 is the oligonucleotide as PCR sense primer designed from the nucleotide sequence of the 5'-flanking region of the Bacillus subtilis gene, aprX.

Example 4

Construction of an aprX Gene-Deleted Strain

Replacement with a Spectinomycin Resistance Gene

An aprX gene-deleted strain was constructed by a double crossover method using a DNA fragment for introducing deletion prepared by a SOE (splicing by overlap extension)-PCR method (Gene, 77: 61 (1989)). Using the primer sets of aprX+5F and aprX+563R, and aprX+775F and aprX+1320R shown in Table 2, a 5' terminal 558-bp fragment (F) containing the upstream of the aprX gene and a 3' terminal 545-bp fragment (G), respectively, were prepared employing as a template the genome DNA extracted from the Bacillus subtilis strain 168. Also, a spectinomycin resistance gene region was excised from the plasmid pDG1727 (Gene, 167: 335 (1995)) at the BamHI and XhoI restriction enzyme cleavage points and inserted into the BamHI and XhoI restriction enzyme cleavage points of pBluescript II SK(+) (from Stratagene) to construct pBlueSPR. Using the DNA of the PBlueSPR as a template, the spectinomycin resistance gene region (H) was amplified employing the primer set of PB-M13-20 and PB-M13Rev (Table 1). Using the DNA fragments of (F), (G), and (H) as templates, a DNA fragment in which (E), (H), and (G) were linked together in that order was then prepared by an SOE-PCR method employing the primer set of aprX+5F and aprX+1320R. Using the prepared DNA fragment, the Bacillus subtilis strain 168 was transformed by a competent cell transformation method, followed by isolating as transformants colonies having grown on an LB agar medium containing spectinomycin (100 µg/mL). The genome of the resultant transformant was extracted to confirm by PCR that the aprX gene was deleted and replaced with the spectinomycin resistance gene. As described above, a strain containing deletion of the *Bacillus subtilis* aprX gene was constructed and designated as strain Δ aprX(Sp).

Example 5

Construction of a Protease Genes Nonuple-Deleted Strain Containing Deletion of the aprX Gene Using the DNA fragment in which (E), (H), and (G) were linked together in that order as shown in Example 4, the protease genes octuple-deleted strain (Example 3, the strain Kao8) was transformed by a competent cell transformation method, followed by isolating as transformants colonies having grown on an LB agar medium containing spectinomycin (100 μg/mL). The genome of the resultant transformant was extracted to confirm by PCR that the aprX gene was deleted and replaced with the spectinomycin resistance gene. As described above, a strain containing deletion of the *Bacillus subtilis* aprX gene in addition to multiple deletion of the 8 genes (aprE, nprB, nprE, bpr, vpr, mpr, epr, wprA) was constructed and designated as strain Kao9.

Example 6

Figure 3:
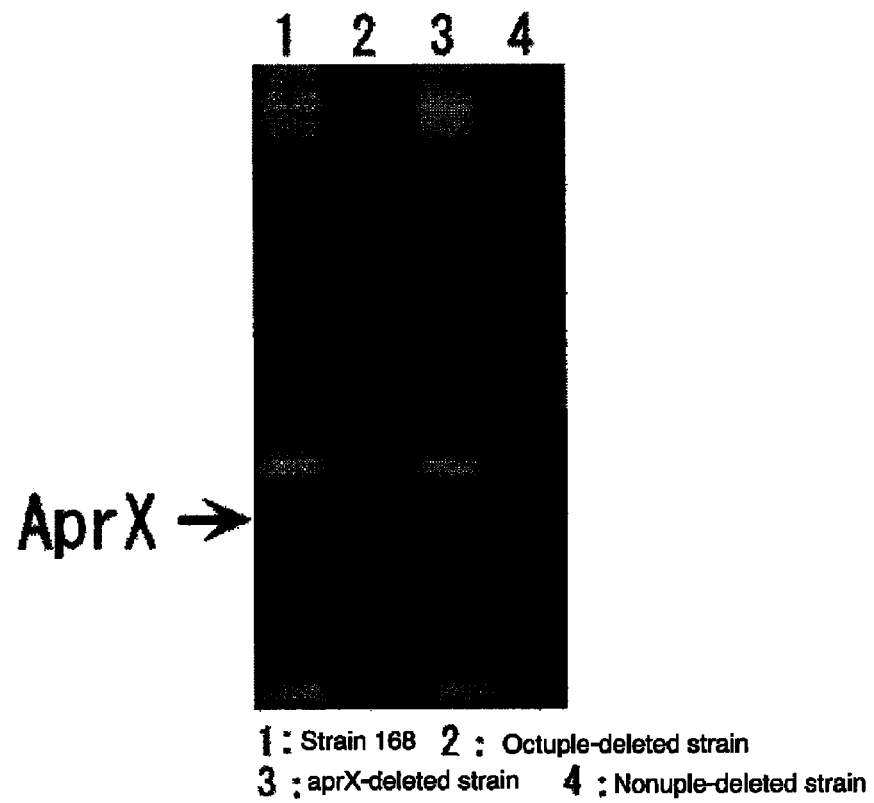
FIG. 3 is a set of photographs showing the results of examining protease activities in the culture supernatant fractions of an aprX gene-deleted strain and a protease genes nonuple-deleted strain (strain Kao 9) and, as controls, of the wild-type *Bacillus subtilis* strain 168 and a protease genes octuple-deleted strain (strain Kao 8), using protease zymograms.

Zymogram Analysis of Protease from the Protease Genes Nonuple-Deleted Strain Containing Deletion of the aprX Gene The gene-deleted strains obtained in Examples 1 to 5 and, as a control, the *Bacillus subtilis* strain 168 were each cultured for 100 hours, and the culture solution was centrifuged at 10,000 rpm for 5 minutes, followed by solubilizing the supernatant to 1× sample buffer (62.5 mM Tris-HCl (pH 6.8), 5% 2-mercaptoethanol, 2% SDS, 5% sucrose, 0.002% BPB (Bromophenol blue)) to make a sample for protease zymography. The sample was subjected to 12% SDS-PAGE containing 0.1% gelatin without boiling, then shaken in renaturation buffer (2.5% Triton X-100) at room temperature for 30 minutes, and further shaken in zymogram developing buffer (50 mM Tris-HCl (pH 8.5), 200 mM NaCl, 5 mM CaCl2, 0.02% Brij35) at room temperature for 30 minutes. The replacement with the zymogram developing buffer was again performed, followed by incubation at 37° C. for 12 hours before staining the gel with CBB (Coomassie stain solution). The zymogram analysis of protease was carried out by the foregoing method (FIG. 3). As a result, a protease activity band was detected even in the octuple-deleted strain (strain Kao8) but disappeared in the aprX gene-deleted strain, demonstrating that the protease activity remaining in the strain Kao8 was that of AprX. No protease activity band was also detected in the protease genes (including aprX) nonuple-deleted strain (strain Kao9).

Example 7

Production of Alkaline Cellulase

Into each of the gene-deleted strains obtained in Examples 1 to 5 and, as a control, the *Bacillus subtilis* strain 168 was introduced, by a protoplast transformation method, a recombinant plasmid, pHY-S237, in which a fragment (3.1 kb) of an alkaline cellulase gene derived from the *Bacillus* sp. strain KSM-S237 (Japanese Patent Laid-Open No. 2000-210081, SEQ ID NO: 1) was inserted into the BamHI restriction enzyme cleavage point of the shuttle vector pHY300PLK. The resultant strain was subjected to shaking culture in 5 mL of an LB medium overnight at 30° C., followed by inoculating 0.03 mL of the culture solution into 30 mL of 2×L-maltose medium (2% tryptone, 1% yeast extract, 1% NaCl, 7.5% maltose, 7.5 ppm manganese sulfate 4- to 5-hydrate, 15 ppm tetracycline) before shaking culture at 30° C. for 4 days. After culture, an alkaline cellulase activity was measured for the supernatant of the culture solution from which microbial cells were removed by centrifugation to determine the amount of alkaline cellulase secretion-produced extracellularly by the culture. As a result, as shown in Table 4, the use of each of the aprX gene-deleted strain ΔaprX(Sp) and the protease genes multiple-deleted strain Kao9 led to high secretory production of alkaline cellulase compared to that of the strain 168 (wild type) as a control.

TABLE 4

| Strain name | Deleted protease gene | Secretory production of alkaline cellulase (Relative value) |
| --- | --- | --- |
| Strain Kao9 | aprE nprB nprE bpr vpr mpr epr wprA aprX | 113 |
| Strain ΔaprX (Sp) | aprX | 108 |
| Strain 168 | None | 100 |

Example 8

Production of the Human Type B Hepatitis Virus Antigen Recognition Domain PreS2 Using the Strains Kao8 and Kao9

Figure 4:
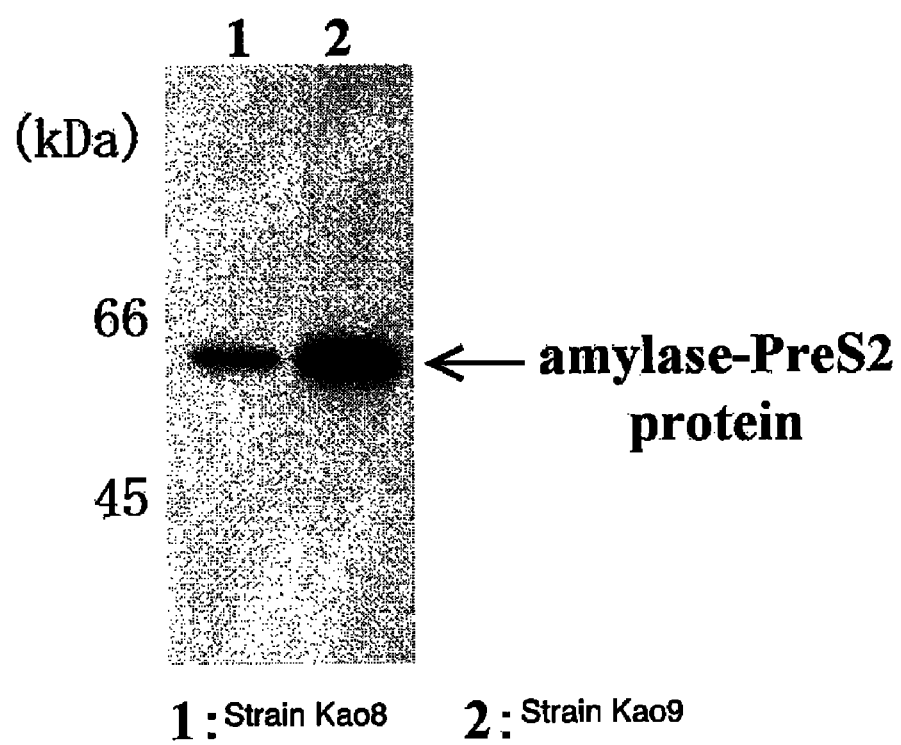
FIG. 4 is a set of photographs showing the results of examining the production of an amylase-PreS2 fusion protein in a protease genes nonuple-deleted strain (strain Kao 9) and, as a control, in a protease genes octuple-deleted strain (strain Kao 8), by Western blotting using anti-PreS2 antibody.

A recombinant plasmid, pTUBE52-preS2 (Appl. Microbiol. Biotechnol., 40: 341 (1993)), was introduced into the strains Kao8 and Kao9 obtained in Examples 3 and 5 by a conventional competent cell transformation method. The plasmid had an inserted DNA fragment (165 bp) in which the fragment of the human type B hepatitis virus antigen recognition domain PreS2 is linked downstream of the gene region encoding the N-terminal 522 amino acids of amylase derived from *Bacillus subtilis*. The resultant transformant strain was subjected to shaking culture overnight at 30° C., followed by inoculating 0.03 mL of the culture solution into 30 mL of 2×L-maltose medium (2% tryptone, 1% yeast extract, 1% NaCl, 7.5% maltose, 7.5 ppm manganese sulfate 4- to 5-hydrate, 15 ppm tetracycline) before shaking culture at 30° C. for 100 hours. After culture, cell bodies were removed by centrifugation, followed by determining the mass of the amylase-PreS2 protein in the resultant culture supernatant by Western blotting analysis using anti-PreS2 antibody (from Institute of Immunology Co., Ltd.). The culture supernatant was first solubilized into 1× sample buffer (62.5 mM Tris-HCl (pH 6.8), 5% 2-mercaptoethanol, 2% SDS, 5% sucrose, 0.002% BPB (Bromophenol blue)), subjected to 10% SDS-PAGE, and then blotted on PVDF (polyvinyl difluoridine membrane: from Immobilon; 0.45 μm pore size; from Millipore). Anti-preS2 antibody (Hyb-5520: from Institute of Immunology Co., Ltd.) was used as a primary antibody. A peroxidase-labeled anti-mouse IgG antibody (from Amersham Pharmacia Biotech) was used as a secondary antibody. Detection was performed with an ECL Plus Western blotting reagent pack (RPN2124; from Amersham Pharmacia Biotech). As a result, as shown in FIG. 4, an evidently intense amylase-PreS2 band was detected for the protease genes nonuple-deleted strain (strain Kao9) compared to that for the octuple-deleted strain (strain Kao8), showing greatly enhanced production of amylase-PreS2 due to deletion of aprX in the nonuple-deleted strain.

Example 9

Construction of a Strain Containing Deletion of the Three Genes aprE, nprE and aprX A microorganism was constructed containing deletion of total 3 types of protease genes, the aprX gene as well as the aprE and nprE genes encoding two major extracellular proteases. pUC118-CmrΔaprE, a plasmid for deleting the aprE gene, was constructed as described in Examples 1 and 2, followed by the introduction of the constructed plasmid into the genome DNA of the Bacillus subtilis strain 168 and the subsequent deletion of the aprE gene through intragenomic homologous recombination to provide an aprE gene single-deleted strain. A protease genes triple-deleted strain containing deletion of the aprE, nprE and aprX genes was then constructed as described in Example 3, and designated as strain Kao3. In this respect, the correspondence is shown in Table 3 between a primer used in deleting the aprX gene for construction of the strain Kao3 and primers employed in deleting the other protease genes.

Example 10

Production of the Human Type B Hepatitis Virus Antigen Recognition Domain PreS2 Using the Strain Kao3

Figure 5:
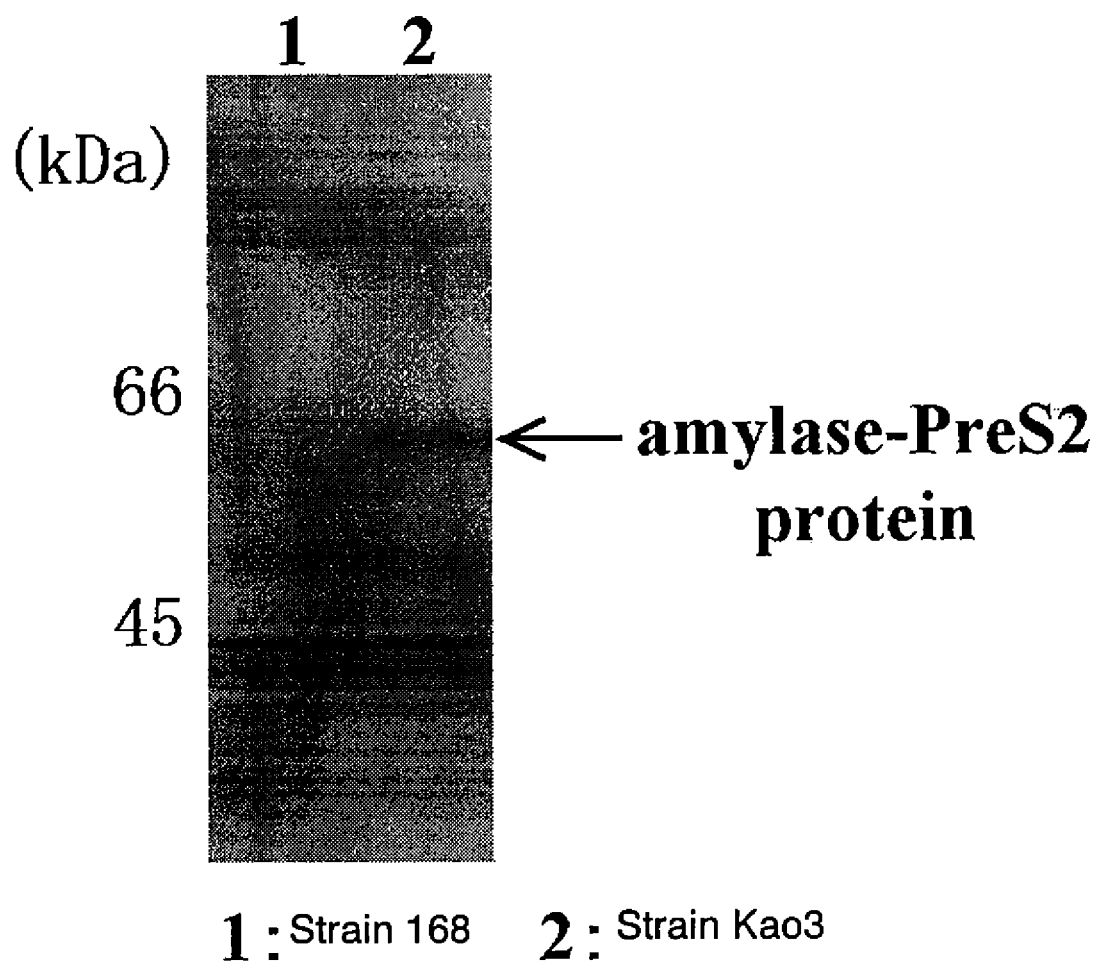
FIG. 5 is a set of photographs showing the results of examining the production of an amylase-PreS2 fusion protein in a protease genes triple-deleted strain (strain Kao 3) and, as a control, in the wild-type *Bacillus subtilis* strain 168, by Western blotting using anti-PreS2 antibody.

As described in Example 8, pRUBE52-preS2, a plasmid for producing amylase-PreS2, was introduced, by a conventional competent cell transformation method, into the strain Kao3 obtained in Example 9 and, as a control, the *Bacillus subtilis* strain 168. The resultant transformant strain was subjected to shaking culture overnight at 30° C., followed by inoculating 0.03 mL of the culture solution into 30 mL of 2×L-maltose medium (2% tryptone, 1% yeast extract, 1% NaCl, 7.5% maltose, 7.5 ppm manganese sulfate 4- to 5-hydrate, 15 ppm tetracycline) before shaking culture at 30° C. for 25 hours. After culture, cell bodies were removed by centrifugation, followed by determining the mass of the amylase-PreS2 protein in the resultant culture supernatant by Western blotting analysis using anti-PreS2 antibody (from Institute of Immunology Co., Ltd.). As shown in FIG. 5, an amylase-PreS2 band, which was not observed for the strain 168 (wild type) as a control, was detected for the protease genes triple-deleted strain, demonstrating enhanced production of amylase-PreS2 in the triple-deleted strain.

The invention claimed is:

1. A recombinant microorganism of the genus *Bacillus*, comprising a gene encoding a heterologous protein or polypeptide that is secreted by said recombinant microorganism, wherein the aprX gene of said recombinant microorganism is identified by the primers set forth in SEQ IDs NOs:50 and 51, or identified by the primers set forth in SEQ IDs NOs:52 and 53, or identified by the primers set forth in SEQ IDs NOs:50 and 53, and has been deleted or knocked out.

2. The recombinant microorganism according to claim 1, wherein one or more protease-encoding genes that are different than the aprX gene have been deleted or knocked out.

3. The recombinant microorganism according to claim 2, wherein the one or more protease-encoding genes that are different than the aprX gene is selected from the group consisting of the aprE, nprB, nprE, bpr, vpr, mpr, epr and wprA genes.

4. The recombinant microorganism according to claim 3, wherein the one or more protease-encoding genes that are different than the aprX gene are the aprE and nprE genes.

5. The recombinant microorganism according to claim 3, wherein the protease-encoding genes that are different than the aprX gene are the aprE, nprB, nprE, bpr, vpr, mpr, epr and wprA genes.

6. The recombinant microorganism according to claim 1, wherein the microorganism is *Bacillus subtilis*.

7. The recombinant microorganism according to claim 1, wherein said recombinant microorganism further comprises at least one region that is ligated upstream of and linked to the gene encoding the heterologous protein or polypeptide and wherein said region is selected from a transcription initiation control region, a translation initiation control region, and a secretion signal region.

8. The recombinant microorganism according to claim 7, wherein said at least one region includes a transcription initiation control region, a translation initiation control region, and a secretion signal region.

9. The recombinant microorganism according to claim 7, wherein the secretion signal region is from a cellulase gene of a bacteria of the genus *Bacillus* and the transcription initiation control region and translation initiation control region are from a 0.6 kb to a 1 kb region upstream of the cellulase gene.

10. The recombinant microorganism according to claim 8, wherein the transcription initiation control region, the translation initiation control region, and the secretion signal region are
   the nucleotide sequence of base numbers 1 to 659 of a cellulase gene of SEQ ID NO:1;
   the nucleotide sequence of base numbers 1 to 696 of a cellulase gene of SEQ ID NO:3;
   a DNA fragment having a nucleotide sequence having at least 70% homology with either of these nucleotide sequences; or
   a DNA fragment having a nucleotide sequence lacking a portion of any one of these nucleotide sequences,
   wherein the regions function in the transcription and translation of the gene encoding the heterologous protein or polypeptide of interest and in the secretion of a product thereof.

11. A method for producing a protein or polypeptide, said method comprising:
   i) inoculating a medium with the recombinant microorganism of any one of claims 1-10;
   ii) growing the resulting culture of recombinant microorganisms;
   iii) collecting the protein or polypeptide from the culture; and
   iv) purifying the protein or polypeptide.

12. The recombinant microorganism according to claim 8, wherein the secretion signal region is from a cellulase gene of a bacteria of the genus *Bacillus* and the transcription initiation control region and translation initiation control region are from a 0.6 to 1 kb region upstream of the cellulase gene.

13. A method for producing a protein or polypeptide, said method comprising:
   i) inoculating a medium with the recombinant microorganism of claim 12;
   ii) growing the resulting culture of recombinant microorganisms;
   iii) collecting the protein or polypeptide from the culture; and
   iv) purifying the protein or polypeptide.

14. A composition comprising:
   a) a recombinant organism according to claim 1;
   b) a culture medium; and
   c) a heterologous protein or polypeptide secreted into the culture medium by the recombinant microorganism.

15. A method for enhancing the yield of a heterologous protein, said method comprising:
   i) culturing the recombinant microorganism of claim 1;
   ii) obtaining an amount of protein that is greater compared to a host microorganism of the genus *Bacillus* in which the aprX gene has not been deleted or knocked out.

16. A method for producing a recombinant microorganism, said method comprising:
   i) providing a host microorganism of the genus *Bacillus*;
   ii) deleting or inactivating the aprX gene in said host microorganism; and
   iii) introducing into said host microorganism a gene encoding a desired protein or polypeptide,
   wherein said aprX gene is identified by the primers set forth in SEQ IDs NOs:50 and 51, or identified by the primers set forth in SEQ IDs NOs:52 and 53, or identified by the primers set forth in SEQ IDs NOs:50 and 53, and wherein said desired protein or polypeptide is secreted by said recombinant microorganism.

* * * * *

SEQUENCE LISTING

```
<160> NUMBER OF SEQ ID NOS: 61

<210> SEQ ID NO 1
<211> LENGTH: 3150
<212> TYPE: DNA
<213> ORGANISM: Bacillus sp. KSM-S237
<220> FEATURE:
<221> NAME/KEY: CDS
<222> LOCATION: (573)..(3044)
<220> FEATURE:
<221> NAME/KEY: sig_peptide
<222> LOCATION: (573)..(659)
<220> FEATURE:
<221> NAME/KEY: mat_peptide
<222> LOCATION: (660)..()

<400> SEQUENCE: 1
gatttgccga tgcaacaggc ttatatttag aggaaatttc ttttttaaatt gaatacggaa      60 taaaatcagg taaacaggtc ctgattttat tttttttgagt tttttagaga actgaagatt     120
gaaataaaag tagaagacaa aggacataag aaaattgcat tagttttaat tatagaaaac     180 gccttttttat aattatttat acctagaacg aaaatactgt ttcgaaagcg gtttactata     240
aaaccttata ttccggctct tttttaaaac aggggggtaaa aattcactct agtattctaa     300
tttcaacatg ctataataaa tttgtaagac gcaatatgca tctcttttttt tacgatatat     360 gtaagcggtt aaccttgtgc tatatgccga tttaggaagg ggggtagatt gagtcaagta     420
gtaataatat agataactta taagttgttg agaagcagga gagcatctgg gttactcaca     480 agtttttttta aaactttaac gaaagcactt tcggtaatgc ttatgaattt agctatttga     540
ttcaattact ttaaaaatat ttaggaggta at atg atg tta aga aag aaa aca      593
                                   Met Met Leu Arg Lys Lys Thr
                                                        -25 aag cag ttg att tct tcc att ctt att tta gtt tta ctt cta tct tta      641
Lys Gln Leu Ile Ser Ser Ile Leu Ile Leu Val Leu Leu Leu Ser Leu
       -20              -15                   -10
```

| | | | | | | | | | | | | | | | | |
|---|---|---|---|---|---|---|---|---|---|---|---|---|---|---|---|---|
| ttt | ccg | gca | gct | ctt | gca | gca | gaa | gga | aac | act | cgt | gaa | gac | aat | ttt | 689 |
| Phe | Pro | Ala | Ala | Leu | Ala | Ala | Glu | Gly | Asn | Thr | Arg | Glu | Asp | Asn | Phe | |
| -5 | | | -1 | 1 | | | | 5 | | | | | | | 10 | |
| aaa | cat | tta | tta | ggt | aat | gac | aat | gtt | aaa | cgc | cct | tct | gag | gct | ggc | 737 |
| Lys | His | Leu | Leu | Gly | Asn | Asp | Asn | Val | Lys | Arg | Pro | Ser | Glu | Ala | Gly | |
| | | | | 15 | | | | | 20 | | | | | 25 | | |
| gca | tta | caa | tta | caa | gaa | gtc | gat | gga | caa | atg | aca | tta | gta | gat | caa | 785 |
| Ala | Leu | Gln | Leu | Gln | Glu | Val | Asp | Gly | Gln | Met | Thr | Leu | Val | Asp | Gln | |
| | | | 30 | | | | | 35 | | | | 40 | | | | |
| cat | gga | gaa | aaa | att | caa | tta | cgt | gga | atg | agt | aca | cac | gga | tta | cag | 833 |
| His | Gly | Glu | Lys | Ile | Gln | Leu | Arg | Gly | Met | Ser | Thr | His | Gly | Leu | Gln | |
| | | | 45 | | | | | 50 | | | | | 55 | | | |
| tgg | ttt | cct | gag | atc | ttg | aat | gat | aac | gca | tac | aaa | gct | ctt | tct | aac | 881 |
| Trp | Phe | Pro | Glu | Ile | Leu | Asn | Asp | Asn | Ala | Tyr | Lys | Ala | Leu | Ser | Asn | |
| | 60 | | | | | 65 | | | | | 70 | | | | | |
| gat | tgg | gat | tcc | aat | atg | att | cgt | ctt | gct | atg | tat | gta | ggt | gaa | aat | 929 |
| Asp | Trp | Asp | Ser | Asn | Met | Ile | Arg | Leu | Ala | Met | Tyr | Val | Gly | Glu | Asn | |
| 75 | | | | | 80 | | | | | 85 | | | | | 90 | |
| ggg | tac | gct | aca | aac | cct | gag | tta | atc | aaa | caa | aga | gtg | att | gat | gga | 977 |
| Gly | Tyr | Ala | Thr | Asn | Pro | Glu | Leu | Ile | Lys | Gln | Arg | Val | Ile | Asp | Gly | |
| | | | | 95 | | | | | 100 | | | | | 105 | | |
| att | gag | tta | gcg | att | gaa | aat | gac | atg | tat | gtt | att | gtt | gac | tgg | cat | 1025 |
| Ile | Glu | Leu | Ala | Ile | Glu | Asn | Asp | Met | Tyr | Val | Ile | Val | Asp | Trp | His | |
| | | | 110 | | | | | 115 | | | | | 120 | | | |
| gtt | cat | gcg | cca | ggt | gat | cct | aga | gat | cct | gtt | tat | gca | ggt | gct | aaa | 1073 |
| Val | His | Ala | Pro | Gly | Asp | Pro | Arg | Asp | Pro | Val | Tyr | Ala | Gly | Ala | Lys | |
| | | 125 | | | | | 130 | | | | | 135 | | | | |
| gat | ttc | ttt | aga | gaa | att | gca | gct | tta | tac | cct | aat | aat | cca | cac | att | 1121 |
| Asp | Phe | Phe | Arg | Glu | Ile | Ala | Ala | Leu | Tyr | Pro | Asn | Asn | Pro | His | Ile | |
| | 140 | | | | | 145 | | | | | 150 | | | | | |
| att | tat | gag | tta | gcg | aat | gag | ccg | agt | agt | aat | aat | aat | ggt | gga | gca | 1169 |
| Ile | Tyr | Glu | Leu | Ala | Asn | Glu | Pro | Ser | Ser | Asn | Asn | Asn | Gly | Gly | Ala | |
| 155 | | | | | 160 | | | | | 165 | | | | | 170 | |
| ggg | att | ccg | aat | aac | gaa | gaa | ggt | tgg | aaa | gcg | gta | aaa | gaa | tat | gct | 1217 |
| Gly | Ile | Pro | Asn | Asn | Glu | Glu | Gly | Trp | Lys | Ala | Val | Lys | Glu | Tyr | Ala | |
| | | | | 175 | | | | | 180 | | | | | 185 | | |
| gat | cca | att | gta | gaa | atg | tta | cgt | aaa | agc | ggt | aat | gca | gat | gac | aac | 1265 |
| Asp | Pro | Ile | Val | Glu | Met | Leu | Arg | Lys | Ser | Gly | Asn | Ala | Asp | Asp | Asn | |
| | | | 190 | | | | | 195 | | | | | 200 | | | |
| att | atc | att | gtt | ggt | agt | cca | aac | tgg | agt | cag | cgt | ccg | gac | tta | gca | 1313 |
| Ile | Ile | Ile | Val | Gly | Ser | Pro | Asn | Trp | Ser | Gln | Arg | Pro | Asp | Leu | Ala | |
| | | 205 | | | | | 210 | | | | | 215 | | | | |
| gct | gat | aat | cca | att | gat | gat | cac | cat | aca | atg | tat | act | gtt | cac | ttc | 1361 |
| Ala | Asp | Asn | Pro | Ile | Asp | Asp | His | His | Thr | Met | Tyr | Thr | Val | His | Phe | |
| | 220 | | | | | 225 | | | | | 230 | | | | | |
| tac | act | ggt | tca | cat | gct | gct | tca | act | gaa | agc | tat | ccg | tct | gaa | act | 1409 |
| Tyr | Thr | Gly | Ser | His | Ala | Ala | Ser | Thr | Glu | Ser | Tyr | Pro | Ser | Glu | Thr | |
| 235 | | | | | 240 | | | | | 245 | | | | | 250 | |
| cct | aac | tct | gaa | aga | gga | aac | gta | atg | agt | aac | act | cgt | tat | gcg | tta | 1457 |
| Pro | Asn | Ser | Glu | Arg | Gly | Asn | Val | Met | Ser | Asn | Thr | Arg | Tyr | Ala | Leu | |
| | | | | 255 | | | | | 260 | | | | | 265 | | |
| gaa | aac | gga | gta | gcg | gta | ttt | gca | aca | gag | tgg | gga | acg | agt | caa | gct | 1505 |
| Glu | Asn | Gly | Val | Ala | Val | Phe | Ala | Thr | Glu | Trp | Gly | Thr | Ser | Gln | Ala | |
| | | | 270 | | | | | 275 | | | | | 280 | | | |
| agt | gga | gac | ggt | ggt | cct | tac | ttt | gat | gaa | gca | gat | gta | tgg | att | gaa | 1553 |
| Ser | Gly | Asp | Gly | Gly | Pro | Tyr | Phe | Asp | Glu | Ala | Asp | Val | Trp | Ile | Glu | |
| | | 285 | | | | | 290 | | | | | 295 | | | | |
| ttt | tta | aat | gaa | aac | aac | att | agc | tgg | gct | aac | tgg | tct | tta | acg | aat | 1601 |
| Phe | Leu | Asn | Glu | Asn | Asn | Ile | Ser | Trp | Ala | Asn | Trp | Ser | Leu | Thr | Asn | |
| | 300 | | | | | 305 | | | | | 310 | | | | | |

```
aaa aat gaa gta tct ggt gca ttt aca cca ttc gag tta ggt aag tct    1649
Lys Asn Glu Val Ser Gly Ala Phe Thr Pro Phe Glu Leu Gly Lys Ser
315                 320                 325                 330 aac gca acc aat ctt gac cca ggt cca gat cat gtg tgg gca cca gaa    1697
Asn Ala Thr Asn Leu Asp Pro Gly Pro Asp His Val Trp Ala Pro Glu
            335                 340                 345 gaa tta agt ctt tct gga gaa tat gta cgt gct cgt att aaa ggt gtg    1745
Glu Leu Ser Leu Ser Gly Glu Tyr Val Arg Ala Arg Ile Lys Gly Val
        350                 355                 360 aac tat gag cca atc gac cgt aca aaa tac acg aaa gta ctt tgg gac    1793
Asn Tyr Glu Pro Ile Asp Arg Thr Lys Tyr Thr Lys Val Leu Trp Asp
    365                 370                 375 ttt aat gat gga acg aag caa gga ttt gga gtg aat tcg gat tct cca    1841
Phe Asn Asp Gly Thr Lys Gln Gly Phe Gly Val Asn Ser Asp Ser Pro
380                 385                 390 aat aaa gaa ctt att gca gtt gat aat gaa aac aac act ttg aaa gtt    1889
Asn Lys Glu Leu Ile Ala Val Asp Asn Glu Asn Asn Thr Leu Lys Val
395                 400                 405                 410 tcg gga tta gat gta agt aac gat gtt tca gat ggc aac ttc tgg gct    1937
Ser Gly Leu Asp Val Ser Asn Asp Val Ser Asp Gly Asn Phe Trp Ala
            415                 420                 425 aat gct cgt ctt tct gcc aac ggt tgg gga aaa agt gtt gat att tta    1985
Asn Ala Arg Leu Ser Ala Asn Gly Trp Gly Lys Ser Val Asp Ile Leu
        430                 435                 440 ggt gct gag aag ctt aca atg gat gtt att gtt gat gaa cca acg acg    2033
Gly Ala Glu Lys Leu Thr Met Asp Val Ile Val Asp Glu Pro Thr Thr
    445                 450                 455 gta gct att gcg gcg att cca caa agt agt aaa agt gga tgg gca aat    2081
Val Ala Ile Ala Ala Ile Pro Gln Ser Ser Lys Ser Gly Trp Ala Asn
460                 465                 470 cca gag cgt gct gtt cga gtg aac gcg gaa gat ttt gtc cag caa acg    2129
Pro Glu Arg Ala Val Arg Val Asn Ala Glu Asp Phe Val Gln Gln Thr
475                 480                 485                 490 gac ggt aag tat aaa gct gga tta aca att aca gga gaa gat gct cct    2177
Asp Gly Lys Tyr Lys Ala Gly Leu Thr Ile Thr Gly Glu Asp Ala Pro
            495                 500                 505 aac cta aaa aat atc gct ttt cat gaa gaa gat aac aat atg aac aac    2225
Asn Leu Lys Asn Ile Ala Phe His Glu Glu Asp Asn Asn Met Asn Asn
        510                 515                 520 atc att ctg ttc gtg gga act gat gca gct gac gtt att tac tta gat    2273
Ile Ile Leu Phe Val Gly Thr Asp Ala Ala Asp Val Ile Tyr Leu Asp
    525                 530                 535 aac att aaa gta att gga aca gaa gtt gaa att cca gtt gtt cat gat    2321
Asn Ile Lys Val Ile Gly Thr Glu Val Glu Ile Pro Val Val His Asp
540                 545                 550 cca aaa gga gaa gct gtt ctt cct tct gtt ttt gaa gac ggt aca cgt    2369
Pro Lys Gly Glu Ala Val Leu Pro Ser Val Phe Glu Asp Gly Thr Arg
555                 560                 565                 570 caa ggt tgg gac tgg gct gga gag tct ggt gtg aaa aca gct tta aca    2417
Gln Gly Trp Asp Trp Ala Gly Glu Ser Gly Val Lys Thr Ala Leu Thr
            575                 580                 585 att gaa gaa gca aac ggt tct aac gcg tta tca tgg gaa ttt gga tat    2465
Ile Glu Glu Ala Asn Gly Ser Asn Ala Leu Ser Trp Glu Phe Gly Tyr
        590                 595                 600 cca gaa gta aaa cct agt gat aac tgg gca aca gct cca cgt tta gat    2513
Pro Glu Val Lys Pro Ser Asp Asn Trp Ala Thr Ala Pro Arg Leu Asp
    605                 610                 615 ttc tgg aaa tct gac ttg gtt cgc ggt gag aat gat tat gta gct ttt    2561
Phe Trp Lys Ser Asp Leu Val Arg Gly Glu Asn Asp Tyr Val Ala Phe
```

```
                620                 625                 630
gat ttc tat cta gat cca gtt cgt gca aca gaa ggc gca atg aat atc      2609
Asp Phe Tyr Leu Asp Pro Val Arg Ala Thr Glu Gly Ala Met Asn Ile
635                 640                 645                 650 aat tta gta ttc cag cca cct act aac ggg tat tgg gta caa gca cca      2657
Asn Leu Val Phe Gln Pro Pro Thr Asn Gly Tyr Trp Val Gln Ala Pro
                655                 660                 665 aaa acg tat acg att aac ttt gat gaa tta gag gaa gcg aat caa gta      2705
Lys Thr Tyr Thr Ile Asn Phe Asp Glu Leu Glu Glu Ala Asn Gln Val
            670                 675                 680 aat ggt tta tat cac tat gaa gtg aaa att aac gta aga gat att aca      2753
Asn Gly Leu Tyr His Tyr Glu Val Lys Ile Asn Val Arg Asp Ile Thr
        685                 690                 695 aac att caa gat gac acg tta cta cgt aac atg atg atc att ttt gca      2801
Asn Ile Gln Asp Asp Thr Leu Leu Arg Asn Met Met Ile Ile Phe Ala
    700                 705                 710 gat gta gaa agt gac ttt gca ggg aga gtc ttt gta gat aat gtt cgt      2849
Asp Val Glu Ser Asp Phe Ala Gly Arg Val Phe Val Asp Asn Val Arg
715                 720                 725                 730 ttt gag ggg gct gct act act gag ccg gtt gaa cca gag cca gtt gat      2897
Phe Glu Gly Ala Ala Thr Thr Glu Pro Val Glu Pro Glu Pro Val Asp
                735                 740                 745 cct ggc gaa gag acg cca cct gtc gat gag aag gaa gcg aaa aaa gaa      2945
Pro Gly Glu Glu Thr Pro Pro Val Asp Glu Lys Glu Ala Lys Lys Glu
            750                 755                 760 caa aaa gaa gca gag aaa gaa gag aaa gaa gca gta aaa gaa gaa aag      2993
Gln Lys Glu Ala Glu Lys Glu Glu Lys Glu Ala Val Lys Glu Glu Lys
        765                 770                 775 aaa gaa gct aaa gaa gaa aag aaa gca gtc aaa aat gag gct aag aaa      3041
Lys Glu Ala Lys Glu Glu Lys Lys Ala Val Lys Asn Glu Ala Lys Lys
    780                 785                 790 aaa taatctatta aactagttat agggttatct aaaggtctga tgtagatctt           3094
Lys
795 ttagataacc ttttcttgc ataactggac acagagttgt tattaaagaa agtaag        3150
```

<210> SEQ ID NO 2
<211> LENGTH: 824
<212> TYPE: PRT
<213> ORGANISM: Bacillus sp. KSM-S237

<400> SEQUENCE: 2

```
Met Met Leu Arg Lys Lys Thr Lys Gln Leu Ile Ser Ser Ile Leu Ile
            -25                 -20                 -15

Leu Val Leu Leu Leu Ser Leu Phe Pro Ala Ala Leu Ala Ala Glu Gly
        -10                 -5                  -1   1

Asn Thr Arg Glu Asp Asn Phe Lys His Leu Leu Gly Asn Asp Asn Val
  5                  10                  15

Lys Arg Pro Ser Glu Ala Gly Ala Leu Gln Leu Glu Val Asp Gly
 20                  25                  30                  35

Gln Met Thr Leu Val Asp Gln His Gly Glu Lys Ile Gln Leu Arg Gly
                40                  45                  50

Met Ser Thr His Gly Leu Gln Trp Phe Pro Glu Ile Leu Asn Asp Asn
            55                  60                  65

Ala Tyr Lys Ala Leu Ser Asn Asp Trp Asp Ser Asn Met Ile Arg Leu
        70                  75                  80

Ala Met Tyr Val Gly Glu Asn Gly Tyr Ala Thr Asn Pro Glu Leu Ile
    85                  90                  95
```

```
Lys Gln Arg Val Ile Asp Gly Ile Glu Leu Ala Ile Glu Asn Asp Met
100                 105                 110                 115

Tyr Val Ile Val Asp Trp His Val His Ala Pro Gly Asp Pro Arg Asp
                120                 125                 130

Pro Val Tyr Ala Gly Ala Lys Asp Phe Phe Arg Glu Ile Ala Ala Leu
                135                 140                 145

Tyr Pro Asn Asn Pro His Ile Ile Tyr Glu Leu Ala Asn Glu Pro Ser
            150                 155                 160

Ser Asn Asn Asn Gly Gly Ala Gly Ile Pro Asn Asn Glu Glu Gly Trp
            165                 170                 175

Lys Ala Val Lys Glu Tyr Ala Asp Pro Ile Val Glu Met Leu Arg Lys
180                 185                 190                 195

Ser Gly Asn Ala Asp Asp Asn Ile Ile Ile Val Gly Ser Pro Asn Trp
                200                 205                 210

Ser Gln Arg Pro Asp Leu Ala Ala Asp Asn Pro Ile Asp Asp His His
                215                 220                 225

Thr Met Tyr Thr Val His Phe Tyr Thr Gly Ser His Ala Ala Ser Thr
            230                 235                 240

Glu Ser Tyr Pro Ser Glu Thr Pro Asn Ser Glu Arg Gly Asn Val Met
245                 250                 255

Ser Asn Thr Arg Tyr Ala Leu Glu Asn Gly Val Ala Val Phe Ala Thr
260                 265                 270                 275

Glu Trp Gly Thr Ser Gln Ala Ser Gly Asp Gly Gly Pro Tyr Phe Asp
                280                 285                 290

Glu Ala Asp Val Trp Ile Glu Phe Leu Asn Glu Asn Asn Ile Ser Trp
                295                 300                 305

Ala Asn Trp Ser Leu Thr Asn Lys Asn Glu Val Ser Gly Ala Phe Thr
                310                 315                 320

Pro Phe Glu Leu Gly Lys Ser Asn Ala Thr Asn Leu Asp Pro Gly Pro
            325                 330                 335

Asp His Val Trp Ala Pro Glu Glu Leu Ser Leu Ser Gly Glu Tyr Val
340                 345                 350                 355

Arg Ala Arg Ile Lys Gly Val Asn Tyr Glu Pro Ile Asp Arg Thr Lys
                360                 365                 370

Tyr Thr Lys Val Leu Trp Asp Phe Asn Asp Gly Thr Lys Gln Gly Phe
                375                 380                 385

Gly Val Asn Ser Asp Ser Pro Asn Lys Glu Leu Ile Ala Val Asp Asn
                390                 395                 400

Glu Asn Asn Thr Leu Lys Val Ser Gly Leu Asp Val Ser Asn Asp Val
            405                 410                 415

Ser Asp Gly Asn Phe Trp Ala Asn Ala Arg Leu Ser Ala Asn Gly Trp
420                 425                 430                 435

Gly Lys Ser Val Asp Ile Leu Gly Ala Glu Lys Leu Thr Met Asp Val
                440                 445                 450

Ile Val Asp Glu Pro Thr Thr Val Ala Ile Ala Ala Ile Pro Gln Ser
                455                 460                 465

Ser Lys Ser Gly Trp Ala Asn Pro Glu Arg Ala Val Arg Val Asn Ala
            470                 475                 480

Glu Asp Phe Val Gln Gln Thr Asp Gly Lys Tyr Lys Ala Gly Leu Thr
            485                 490                 495

Ile Thr Gly Glu Asp Ala Pro Asn Leu Lys Asn Ile Ala Phe His Glu
500                 505                 510                 515
```

-continued

```
Glu Asp Asn Asn Met Asn Asn Ile Ile Leu Phe Val Gly Thr Asp Ala
                520                 525                 530
Ala Asp Val Ile Tyr Leu Asp Asn Ile Lys Val Ile Gly Thr Glu Val
            535                 540                 545
Glu Ile Pro Val Val His Asp Pro Lys Gly Glu Ala Val Leu Pro Ser
        550                 555                 560
Val Phe Glu Asp Gly Thr Arg Gln Gly Trp Asp Trp Ala Gly Glu Ser
    565                 570                 575
Gly Val Lys Thr Ala Leu Thr Ile Glu Glu Ala Asn Gly Ser Asn Ala
580                 585                 590                 595
Leu Ser Trp Glu Phe Gly Tyr Pro Glu Val Lys Pro Ser Asp Asn Trp
                600                 605                 610
Ala Thr Ala Pro Arg Leu Asp Phe Trp Lys Ser Asp Leu Val Arg Gly
            615                 620                 625
Glu Asn Asp Tyr Val Ala Phe Asp Phe Tyr Leu Asp Pro Val Arg Ala
        630                 635                 640
Thr Glu Gly Ala Met Asn Ile Asn Leu Val Phe Gln Pro Pro Thr Asn
    645                 650                 655
Gly Tyr Trp Val Gln Ala Pro Lys Thr Tyr Thr Ile Asn Phe Asp Glu
660                 665                 670                 675
Leu Glu Glu Ala Asn Gln Val Asn Gly Leu Tyr His Tyr Glu Val Lys
                680                 685                 690
Ile Asn Val Arg Asp Ile Thr Asn Ile Gln Asp Asp Thr Leu Leu Arg
            695                 700                 705
Asn Met Met Ile Ile Phe Ala Asp Val Glu Ser Asp Phe Ala Gly Arg
        710                 715                 720
Val Phe Val Asp Asn Val Arg Phe Glu Gly Ala Ala Thr Thr Glu Pro
    725                 730                 735
Val Glu Pro Glu Pro Val Asp Pro Gly Glu Glu Thr Pro Pro Val Asp
740                 745                 750                 755
Glu Lys Glu Ala Lys Lys Glu Gln Lys Glu Ala Glu Lys Glu Glu Lys
                760                 765                 770
Glu Ala Val Lys Glu Glu Lys Lys Glu Ala Lys Glu Glu Lys Lys Ala
            775                 780                 785
Val Lys Asn Glu Ala Lys Lys Lys
        790                 795

<210> SEQ ID NO 3
<211> LENGTH: 3332
<212> TYPE: DNA
<213> ORGANISM: Bacillus sp. KSM-64
<220> FEATURE:
<221> NAME/KEY: CDS
<222> LOCATION: (610)..(3075)
<220> FEATURE:
<221> NAME/KEY: sig_peptide
<222> LOCATION: (610)..(696)
<220> FEATURE:
<221> NAME/KEY: mat_peptide
<222> LOCATION: (697)..()

<400> SEQUENCE: 3
agtacttacc attttagagt caaaagatag aagccaagca ggatttgccg atgcaaccgg     60 cttatatttta gagggaattt cttttttaaat tgaatacgga ataaaatcag gtaaacaggt    120 cctgattta ttttttttgaa ttttttttgag aactaaagat tgaaatagaa gtagaagaca    180
acggacataa gaaaattgta ttagttttaa ttatagaaaa cgcttttcta taattattta    240
```

```
tacctagaac gaaaatactg tttcgaaagc ggtttactat aaaaccttat attccggctc    300
tttttttaaa caggggtgta aaattcactc tagtattcta atttcaacat gctataataa    360
atttgtaaga cgcaatatac atctttttt tatgatattt gtaagcggtt aaccttgtgc    420
tatatgccga tttaggaagg gggtagattg agtcaagtag tcataattta gataacttat    480
aagttgttga gaagcaggag agaatctggg ttactcacaa gttttttaaa acattatcga    540
aagcactttc ggttatgctt atgaatttag ctatttgatt caattacttt aataatttta    600 ggaggtaat atg atg tta aga aag aaa aca aag cag ttg att tct tcc att                     651
         Met Met Leu Arg Lys Lys Thr Lys Gln Leu Ile Ser Ser Ile
             -25                     -20 ctt att tta gtt tta ctt cta tct tta ttt ccg aca gct ctt gca gca                        699
Leu Ile Leu Val Leu Leu Leu Ser Leu Phe Pro Thr Ala Leu Ala Ala
-15             -10                  -5                  -1  1 gaa gga aac act cgt gaa gac aat ttt aaa cat tta tta ggt aat gac                        747
Glu Gly Asn Thr Arg Glu Asp Asn Phe Lys His Leu Leu Gly Asn Asp
            5                   10                  15 aat gtt aaa cgc cct tct gag gct ggc gca tta caa tta caa gaa gtc                        795
Asn Val Lys Arg Pro Ser Glu Ala Gly Ala Leu Gln Leu Gln Glu Val
            20                  25                  30 gat gga caa atg aca tta gta gat caa cat gga gaa aaa att caa tta                        843
Asp Gly Gln Met Thr Leu Val Asp Gln His Gly Glu Lys Ile Gln Leu
        35                  40                  45 cgt gga atg agt aca cac gga tta caa tgg ttt cct gag atc ttg aat                        891
Arg Gly Met Ser Thr His Gly Leu Gln Trp Phe Pro Glu Ile Leu Asn
50              55                  60                  65 gat aac gca tac aaa gct ctt gct aac gat tgg gaa tca aat atg att                        939
Asp Asn Ala Tyr Lys Ala Leu Ala Asn Asp Trp Glu Ser Asn Met Ile
                70                  75                  80 cgt cta gct atg tat gtc ggt gaa aat ggc tat gct tca aat cca gag                        987
Arg Leu Ala Met Tyr Val Gly Glu Asn Gly Tyr Ala Ser Asn Pro Glu
            85                  90                  95 tta att aaa agc aga gtc att aaa gga ata gat ctt gct att gaa aat                       1035
Leu Ile Lys Ser Arg Val Ile Lys Gly Ile Asp Leu Ala Ile Glu Asn
            100                 105                 110 gac atg tat gtc atc gtt gat tgg cat gta cat gca cct ggt gat cct                       1083
Asp Met Tyr Val Ile Val Asp Trp His Val His Ala Pro Gly Asp Pro
        115                 120                 125 aga gat ccc gtt tac gct gga gca gaa gat ttc ttt aga gat att gca                       1131
Arg Asp Pro Val Tyr Ala Gly Ala Glu Asp Phe Phe Arg Asp Ile Ala
130                 135                 140                 145 gca tta tat cct aac aat cca cac att att tat gag tta gcg aat gag                       1179
Ala Leu Tyr Pro Asn Asn Pro His Ile Ile Tyr Glu Leu Ala Asn Glu
            150                 155                 160 cca agt agt aac aat aat ggt gga gct ggg att cca aat aat gaa gaa                       1227
Pro Ser Ser Asn Asn Asn Gly Gly Ala Gly Ile Pro Asn Asn Glu Glu
            165                 170                 175 ggt tgg aat gcg gta aaa gaa tac gct gat cca att gta gaa atg tta                       1275
Gly Trp Asn Ala Val Lys Glu Tyr Ala Asp Pro Ile Val Glu Met Leu
            180                 185                 190 cgt gat agc ggg aac gca gat gac aat att atc att gtg ggt agt cca                       1323
Arg Asp Ser Gly Asn Ala Asp Asp Asn Ile Ile Ile Val Gly Ser Pro
        195                 200                 205 aac tgg agt cag cgt cct gac tta gca gct gat aat cca att gat gat                       1371
Asn Trp Ser Gln Arg Pro Asp Leu Ala Ala Asp Asn Pro Ile Asp Asp
210                 215                 220                 225 cac cat aca atg tat act gtt cac ttc tac act ggt tca cat gct gct                       1419
His His Thr Met Tyr Thr Val His Phe Tyr Thr Gly Ser His Ala Ala
            230                 235                 240
```

```
tca act gaa agc tat ccg cct gaa act cct aac tct gaa aga gga aac    1467
Ser Thr Glu Ser Tyr Pro Pro Glu Thr Pro Asn Ser Glu Arg Gly Asn
        245                 250                 255 gta atg agt aac act cgt tat gcg tta gaa aac gga gta gca gta ttt    1515
Val Met Ser Asn Thr Arg Tyr Ala Leu Glu Asn Gly Val Ala Val Phe
        260                 265                 270 gca aca gag tgg gga act agc caa gca aat gga gat ggt ggt cct tac    1563
Ala Thr Glu Trp Gly Thr Ser Gln Ala Asn Gly Asp Gly Gly Pro Tyr
275                 280                 285 ttt gat gaa gca gat gta tgg att gag ttt tta aat gaa aac aac att    1611
Phe Asp Glu Ala Asp Val Trp Ile Glu Phe Leu Asn Glu Asn Asn Ile
290                 295                 300                 305 agc tgg gct aac tgg tct tta acg aat aaa aat gaa gta tct ggt gca    1659
Ser Trp Ala Asn Trp Ser Leu Thr Asn Lys Asn Glu Val Ser Gly Ala
            310                 315                 320 ttt aca cca ttc gag tta ggt aag tct aac gca aca agt ctt gac cca    1707
Phe Thr Pro Phe Glu Leu Gly Lys Ser Asn Ala Thr Ser Leu Asp Pro
        325                 330                 335 ggg cca gac caa gta tgg gta cca gaa gag tta agt ctt tct gga gaa    1755
Gly Pro Asp Gln Val Trp Val Pro Glu Glu Leu Ser Leu Ser Gly Glu
        340                 345                 350 tat gta cgt gct cgt att aaa ggt gtg aac tat gag cca atc gac cgt    1803
Tyr Val Arg Ala Arg Ile Lys Gly Val Asn Tyr Glu Pro Ile Asp Arg
        355                 360                 365 aca aaa tac acg aaa gta ctt tgg gac ttt aat gat gga acg aag caa    1851
Thr Lys Tyr Thr Lys Val Leu Trp Asp Phe Asn Asp Gly Thr Lys Gln
370                 375                 380                 385 gga ttt gga gtg aat gga gat tct cca gtt gaa gat gta gtt att gag    1899
Gly Phe Gly Val Asn Gly Asp Ser Pro Val Glu Asp Val Val Ile Glu
                390                 395                 400 aat gaa gcg ggc gct tta aaa ctt tca gga tta gat gca agt aat gat    1947
Asn Glu Ala Gly Ala Leu Lys Leu Ser Gly Leu Asp Ala Ser Asn Asp
            405                 410                 415 gtt tct gaa ggt aat tac tgg gct aat gct cgt ctt tct gcc gac ggt    1995
Val Ser Glu Gly Asn Tyr Trp Ala Asn Ala Arg Leu Ser Ala Asp Gly
        420                 425                 430 tgg gga aaa agt gtt gat att tta ggt gct gaa aaa ctt act atg gat    2043
Trp Gly Lys Ser Val Asp Ile Leu Gly Ala Glu Lys Leu Thr Met Asp
    435                 440                 445 gtg att gtt gat gag ccg acc acg gta tca att gct gca att cca caa    2091
Val Ile Val Asp Glu Pro Thr Thr Val Ser Ile Ala Ala Ile Pro Gln
450                 455                 460                 465 ggg cca tca gcc aat tgg gtt aat cca aat cgt gca att aag gtt gag    2139
Gly Pro Ser Ala Asn Trp Val Asn Pro Asn Arg Ala Ile Lys Val Glu
                470                 475                 480 cca act aat ttc gta ccg tta gga gat aag ttt aaa gcg gaa tta act    2187
Pro Thr Asn Phe Val Pro Leu Gly Asp Lys Phe Lys Ala Glu Leu Thr
            485                 490                 495 ata act tca gct gac tct cca tcg tta gaa gct att gcg atg cat gct    2235
Ile Thr Ser Ala Asp Ser Pro Ser Leu Glu Ala Ile Ala Met His Ala
        500                 505                 510 gaa aat aac aac atc aac aac atc att ctt ttt gta gga act gaa ggt    2283
Glu Asn Asn Asn Ile Asn Asn Ile Ile Leu Phe Val Gly Thr Glu Gly
515                 520                 525 gct gat gtt atc tat tta gat aac att aaa gta att gga aca gaa gtt    2331
Ala Asp Val Ile Tyr Leu Asp Asn Ile Lys Val Ile Gly Thr Glu Val
530                 535                 540                 545 gaa att cca gtt gtt cat gat cca aaa gga gaa gct gtt ctt cct tct    2379
Glu Ile Pro Val Val His Asp Pro Lys Gly Glu Ala Val Leu Pro Ser
```

```
                550                555                560
gtt ttt gaa gac ggt aca cgt caa ggt tgg gac tgg gct gga gag tct    2427
Val Phe Glu Asp Gly Thr Arg Gln Gly Trp Asp Trp Ala Gly Glu Ser
            565                570                575 ggt gtg aaa aca gct tta aca att gaa gaa gca aac ggt tct aac gcg    2475
Gly Val Lys Thr Ala Leu Thr Ile Glu Glu Ala Asn Gly Ser Asn Ala
        580                585                590 tta tca tgg gaa ttt gga tac cca gaa gta aaa cct agt gat aac tgg    2523
Leu Ser Trp Glu Phe Gly Tyr Pro Glu Val Lys Pro Ser Asp Asn Trp
595                600                605 gca aca gct cca cgt tta gat ttc tgg aaa tct gac ttg gtt cgc ggt    2571
Ala Thr Ala Pro Arg Leu Asp Phe Trp Lys Ser Asp Leu Val Arg Gly
            610                615                620                625 gaa aat gat tat gta act ttt gat ttc tat cta gat cca gtt cgt gca    2619
Glu Asn Asp Tyr Val Thr Phe Asp Phe Tyr Leu Asp Pro Val Arg Ala
                630                635                640 aca gaa ggc gca atg aat atc aat tta gta ttc cag cca cct act aac    2667
Thr Glu Gly Ala Met Asn Ile Asn Leu Val Phe Gln Pro Pro Thr Asn
            645                650                655 ggg tat tgg gta caa gca cca aaa acg tat acg att aac ttt gat gaa    2715
Gly Tyr Trp Val Gln Ala Pro Lys Thr Tyr Thr Ile Asn Phe Asp Glu
        660                665                670 tta gag gaa gcg aat caa gta aat ggt tta tat cac tat gaa gtg aaa    2763
Leu Glu Glu Ala Asn Gln Val Asn Gly Leu Tyr His Tyr Glu Val Lys
675                680                685 att aac gta aga gat att aca aac att caa gat gac acg tta cta cgt    2811
Ile Asn Val Arg Asp Ile Thr Asn Ile Gln Asp Asp Thr Leu Leu Arg
690                695                700                705 aac atg atg atc att ttt gca gat gta gaa agt gac ttt gca ggg aga    2859
Asn Met Met Ile Ile Phe Ala Asp Val Glu Ser Asp Phe Ala Gly Arg
            710                715                720 gtc ttt gta gat aat gtt cgt ttt gag ggg gct gct act act gag ccg    2907
Val Phe Val Asp Asn Val Arg Phe Glu Gly Ala Ala Thr Thr Glu Pro
                725                730                735 gtt gaa cca gag cca gtt gat cct ggc gaa gag acg ccg cct gtc gat    2955
Val Glu Pro Glu Pro Val Asp Pro Gly Glu Glu Thr Pro Pro Val Asp
        740                745                750 gag aag gaa gcg aaa aaa gaa caa aaa gaa gca gag aaa gaa gag aaa    3003
Glu Lys Glu Ala Lys Lys Glu Gln Lys Glu Ala Glu Lys Glu Glu Lys
755                760                765 gaa gca gta aaa gaa gaa aag aaa gaa gct aaa gaa gaa aag aaa gca    3051
Glu Ala Val Lys Glu Glu Lys Lys Glu Ala Lys Glu Glu Lys Lys Ala
770                775                780                785 atc aaa aat gag gct acg aaa aaa taatctaata aactagttat agggttatct    3105
Ile Lys Asn Glu Ala Thr Lys Lys
                790 aaaggtctga tgcagatctt ttagataacc ttttttgca taactggaca tagaatggtt    3165 attaaagaaa gcaaggtgtt tatacgatat taaaaggta gcgattttaa attgaaacct    3225 ttaataatgt cttgtgatag aatgatgaag taatttaaga gggggaaacg aagtgaaaac    3285 ggaaatttct agtagaagaa aaacagacca agaaatactg caagctt              3332

<210> SEQ ID NO 4
<211> LENGTH: 822
<212> TYPE: PRT
<213> ORGANISM: Bacillus sp. KSM-64

<400> SEQUENCE: 4

Met Met Leu Arg Lys Lys Thr Lys Gln Leu Ile Ser Ser Ile Leu Ile
```

```
                 -25                 -20                 -15
Leu Val Leu Leu Leu Ser Leu Phe Pro Thr Ala Leu Ala Ala Glu Gly
            -10                 -5                  -1  1

Asn Thr Arg Glu Asp Asn Phe Lys His Leu Leu Gly Asn Asp Asn Val
 5                  10                  15

Lys Arg Pro Ser Glu Ala Gly Ala Leu Gln Leu Gln Glu Val Asp Gly
20                  25                  30                  35

Gln Met Thr Leu Val Asp Gln His Gly Glu Lys Ile Gln Leu Arg Gly
                40                  45                  50

Met Ser Thr His Gly Leu Gln Trp Phe Pro Glu Ile Leu Asn Asp Asn
            55                  60                  65

Ala Tyr Lys Ala Leu Ala Asn Asp Trp Glu Ser Asn Met Ile Arg Leu
        70                  75                  80

Ala Met Tyr Val Gly Glu Asn Gly Tyr Ala Ser Asn Pro Glu Leu Ile
    85                  90                  95

Lys Ser Arg Val Ile Lys Gly Ile Asp Leu Ala Ile Glu Asn Asp Met
100                 105                 110                 115

Tyr Val Ile Val Asp Trp His Val His Ala Pro Gly Asp Pro Arg Asp
                120                 125                 130

Pro Val Tyr Ala Gly Ala Glu Asp Phe Phe Arg Asp Ile Ala Ala Leu
            135                 140                 145

Tyr Pro Asn Asn Pro His Ile Ile Tyr Glu Leu Ala Asn Glu Pro Ser
        150                 155                 160

Ser Asn Asn Asn Gly Gly Ala Gly Ile Pro Asn Asn Glu Glu Gly Trp
    165                 170                 175

Asn Ala Val Lys Glu Tyr Ala Asp Pro Ile Val Glu Met Leu Arg Asp
180                 185                 190                 195

Ser Gly Asn Ala Asp Asp Asn Ile Ile Ile Val Gly Ser Pro Asn Trp
                200                 205                 210

Ser Gln Arg Pro Asp Leu Ala Ala Asp Asn Pro Ile Asp Asp His His
            215                 220                 225

Thr Met Tyr Thr Val His Phe Tyr Thr Gly Ser His Ala Ala Ser Thr
        230                 235                 240

Glu Ser Tyr Pro Pro Glu Thr Pro Asn Ser Glu Arg Gly Asn Val Met
    245                 250                 255

Ser Asn Thr Arg Tyr Ala Leu Glu Asn Gly Val Ala Val Phe Ala Thr
260                 265                 270                 275

Glu Trp Gly Thr Ser Gln Ala Asn Gly Asp Gly Pro Tyr Phe Asp
                280                 285                 290

Glu Ala Asp Val Trp Ile Glu Phe Leu Asn Glu Asn Asn Ile Ser Trp
            295                 300                 305

Ala Asn Trp Ser Leu Thr Asn Lys Asn Glu Val Ser Gly Ala Phe Thr
        310                 315                 320

Pro Phe Glu Leu Gly Lys Ser Asn Ala Thr Ser Leu Asp Pro Gly Pro
    325                 330                 335

Asp Gln Val Trp Val Pro Glu Glu Leu Ser Leu Ser Gly Glu Tyr Val
340                 345                 350                 355

Arg Ala Arg Ile Lys Gly Val Asn Tyr Glu Pro Ile Asp Arg Thr Lys
                360                 365                 370

Tyr Thr Lys Val Leu Trp Asp Phe Asn Asp Gly Thr Lys Gln Gly Phe
            375                 380                 385

Gly Val Asn Gly Asp Ser Pro Val Glu Asp Val Val Ile Glu Asn Glu
        390                 395                 400
```

-continued

```
Ala Gly Ala Leu Lys Leu Ser Gly Leu Asp Ala Ser Asn Asp Val Ser
    405                 410                 415

Glu Gly Asn Tyr Trp Ala Asn Ala Arg Leu Ser Ala Asp Gly Trp Gly
420                 425                 430                 435

Lys Ser Val Asp Ile Leu Gly Ala Glu Lys Leu Thr Met Asp Val Ile
                440                 445                 450

Val Asp Glu Pro Thr Thr Val Ser Ile Ala Ala Ile Pro Gln Gly Pro
            455                 460                 465

Ser Ala Asn Trp Val Asn Pro Asn Arg Ala Ile Lys Val Glu Pro Thr
        470                 475                 480

Asn Phe Val Pro Leu Gly Asp Lys Phe Lys Ala Glu Leu Thr Ile Thr
    485                 490                 495

Ser Ala Asp Ser Pro Ser Leu Glu Ala Ile Ala Met His Ala Glu Asn
500                 505                 510                 515

Asn Asn Ile Asn Asn Ile Ile Leu Phe Val Gly Thr Glu Gly Ala Asp
                520                 525                 530

Val Ile Tyr Leu Asp Asn Ile Lys Val Ile Gly Thr Glu Val Glu Ile
            535                 540                 545

Pro Val Val His Asp Pro Lys Gly Glu Ala Val Leu Pro Ser Val Phe
        550                 555                 560

Glu Asp Gly Thr Arg Gln Gly Trp Asp Trp Ala Gly Glu Ser Gly Val
    565                 570                 575

Lys Thr Ala Leu Thr Ile Glu Glu Ala Asn Gly Ser Asn Ala Leu Ser
580                 585                 590                 595

Trp Glu Phe Gly Tyr Pro Glu Val Lys Pro Ser Asp Asn Trp Ala Thr
                600                 605                 610

Ala Pro Arg Leu Asp Phe Trp Lys Ser Asp Leu Val Arg Gly Glu Asn
            615                 620                 625

Asp Tyr Val Thr Phe Asp Phe Tyr Leu Asp Pro Val Arg Ala Thr Glu
        630                 635                 640

Gly Ala Met Asn Ile Asn Leu Val Phe Gln Pro Pro Thr Asn Gly Tyr
    645                 650                 655

Trp Val Gln Ala Pro Lys Thr Tyr Thr Ile Asn Phe Asp Glu Leu Glu
660                 665                 670                 675

Glu Ala Asn Gln Val Asn Gly Leu Tyr His Tyr Glu Val Lys Ile Asn
                680                 685                 690

Val Arg Asp Ile Thr Asn Ile Gln Asp Asp Thr Leu Leu Arg Asn Met
            695                 700                 705

Met Ile Ile Phe Ala Asp Val Glu Ser Asp Phe Ala Gly Arg Val Phe
        710                 715                 720

Val Asp Asn Val Arg Phe Glu Gly Ala Ala Thr Thr Glu Pro Val Glu
    725                 730                 735

Pro Glu Pro Val Asp Pro Gly Glu Glu Thr Pro Pro Val Asp Glu Lys
740                 745                 750                 755

Glu Ala Lys Lys Glu Gln Lys Glu Ala Glu Lys Glu Lys Glu Lys Ala
                760                 765                 770

Val Lys Glu Glu Lys Lys Glu Ala Lys Glu Lys Lys Ala Ile Lys
            775                 780                 785

Asn Glu Ala Thr Lys Lys
        790
```

<210> SEQ ID NO 5
<211> LENGTH: 18

```
<212> TYPE: DNA
<213> ORGANISM: Artificial Sequence
<220> FEATURE:
<223> OTHER INFORMATION: Synthetic oligonucleotide primer

<400> SEQUENCE: 5
ctccggcaga aagggcat                                                  18

<210> SEQ ID NO 6
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 6
cgttcagccg tacaacaagt ttgcaagaca tg                                  32

<210> SEQ ID NO 7
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 7
aacttgttgt acggctgaac gccgtcaaac c                                   31

<210> SEQ ID NO 8
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 8
ctgatctcga cttcgttcag acgggtcgta caatggctg                           39

<210> SEQ ID NO 9
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 9
gaacgaagtc gagatcag                                                  18

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 10
gctgtaatat aaaaaccttc t                                              21

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 11
```

-continued cgacaccata gctttctg 18

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 12
aactaacggg gcaggtta 18

<210> SEQ ID NO 13
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 13
agaatcaatc ccatggtctc acttttccac ttttttgtctt g 41

<210> SEQ ID NO 14
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 14
gtgagaccat gggattgatt ctaatgaaga aagcagacaa g 41

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 15
gggtaattta tctgataggg 20

<210> SEQ ID NO 16
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 16
cttttgcttc ccacaaccga gctgaatttt ctg 33

<210> SEQ ID NO 17
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 17
ctcggttgtg ggaagcaaaa gttgttgttg aaaa 34

<210> SEQ ID NO 18
<211> LENGTH: 39
<212> TYPE: DNA
<213> ORGANISM: Artificial Sequence

```
<220> FEATURE:
<223> OTHER INFORMATION: Synthetic oligonucleotide primer

<400> SEQUENCE: 18
ctgatctcga cttcgttcat cctcattgaa gacggcatc                    39

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 19
ggaacatata tgacacacct                                         20

<210> SEQ ID NO 20
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 20
tgtttggtgt tgagctgtt                                          19

<210> SEQ ID NO 21
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 21
ttcgtgtgaa tccattgttt tctgaatctt ggaa                         34

<210> SEQ ID NO 22
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 22
gaaaacaatg gattcacacg aacggaggat cgt                          33

<210> SEQ ID NO 23
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 23
ctgatctcga cttcgttcct cgtaagaaaa aatacctatt tc                42

<210> SEQ ID NO 24
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 24
ccttgcgaaa gatagggta                                          19
```

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 25
tttttagcag tggtgctc                                          18

<210> SEQ ID NO 26
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 26
catacgcctt cagtaataga gatgtcttgg tc                          32

<210> SEQ ID NO 27
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 27
ctctattact gaaggcgtat gaggctgtcg gc                          32

<210> SEQ ID NO 28
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 28
ctgatctcga cttcgttctt ccaaatgcgc ttcattagga                  40

<210> SEQ ID NO 29
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 29
cttttgagcc cgttcctc                                          18

<210> SEQ ID NO 30
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 30
tgagattgtg gtgacagtg                                         19

<210> SEQ ID NO 31
<211> LENGTH: 33
<212> TYPE: DNA
<213> ORGANISM: Artificial Sequence
<220> FEATURE:
<223> OTHER INFORMATION: Synthetic oligonucleotide primer

```
<400> SEQUENCE: 31
ttaagttttc cgctgatgag tctgttttc gtt                                    33

<210> SEQ ID NO 32
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 32
gactcatcag cggaaaactt aatatgaaca cagaa                                 35

<210> SEQ ID NO 33
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 33
ctgatctcga cttcgttcgt aatcatgaca ccgttttgaa c                          41

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 34
attgcaaccg gctttatcg                                                   19

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 35
ttttgaagac gttcggcga                                                   19

<210> SEQ ID NO 36
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 36
attgtctgtt gctgaagcag cctggaatgc tgtt                                  34

<210> SEQ ID NO 37
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 37
caggctgctt cagcaacaga caatttctta ccta                                  34

<210> SEQ ID NO 38
```

```
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 38
ctgatctcga cttcgttccc tctcttaagt aagcgctg                              38

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 39
tctctttgtt gaaaaacgat a                                                21

<210> SEQ ID NO 40
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 40
aaaaacatcc ctccgcttc                                                   19

<210> SEQ ID NO 41
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 41
tcttcggtca atacaagcag aaagcgaatg at                                    32

<210> SEQ ID NO 42
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 42
tctgcttgta ttgaccgaag aacctttcac tg                                    32

<210> SEQ ID NO 43
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 43
ctgatctcga cttcgttctg ctcggctcat ctggagaaa                             39

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 44
```

```
tttttggcag gcagcctt                                                    18

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 45
ctgtttatta tgggccacga a                                                21

<210> SEQ ID NO 46
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 46
gatcagcttg gggttaatca acgtacaagc ag                                    32

<210> SEQ ID NO 47
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 47
tgattaaccc caagctgatc cacaattttt tgc                                   33

<210> SEQ ID NO 48
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 48
ctgatctcga cttcgttctg attttccaaa cgagctttc                             39

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 49
atgggccatt atgtcatgaa g                                                21

<210> SEQ ID NO 50
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 50
ttgggtactc tatggtac                                                    18

<210> SEQ ID NO 51
<211> LENGTH: 36
<212> TYPE: DNA
```

```
<213> ORGANISM: Artificial Sequence
<220> FEATURE:
<223> OTHER INFORMATION: Synthetic oligonucleotide primer

<400> SEQUENCE: 51
cactggccgt cgttttaccc atgaccatta tcatcg                              36

<210> SEQ ID NO 52
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 52
catggtcata gctgtttcct tatgagcatg tcgctcg                             37

<210> SEQ ID NO 53
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 53
gggaacggaa ttttctgc                                                  18

<210> SEQ ID NO 54
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 54
gtaaaacgac ggccagtg                                                  18

<210> SEQ ID NO 55
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 55
ggaaacagct atgaccatg                                                 19

<210> SEQ ID NO 56
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 56
ttctttatca tcctcatgg                                                 19

<210> SEQ ID NO 57
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 57
tacaaatggt gaacgcagaa aattccgttc                                     30
```

<210> SEQ ID NO 58
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 58 tttctgcgt tcaccatttg taccatagag                                   30

<210> SEQ ID NO 59
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 59
ctgatctcga cttcgttcta acaacctcac ttggcaa                          37

<210> SEQ ID NO 60
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 60
atagatcggc gcctgaaa                                               18

<210> SEQ ID NO 61
<211> LENGTH: 480
<212> TYPE: PRT
<213> ORGANISM: Bacillus sp. KSM-K38

<400> SEQUENCE: 61

Asp Gly Leu Asn Gly Thr Met Met Gln Tyr Tyr Glu Trp His Leu Glu
1               5                   10                  15

Asn Asp Gly Gln His Trp Asn Arg Leu His Asp Ala Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn

-continued

```
            180                 185                 190
Tyr Asp Tyr Leu Leu Gly Ser Asn Ile Asp Phe Ser His Pro Glu Val
        195                 200                 205
Gln Asp Glu Leu Lys Asp Trp Gly Ser Trp Phe Thr Asp Glu Leu Asp
        210                 215                 220
Leu Asp Gly Tyr Arg Leu Asp Ala Ile Lys His Ile Pro Phe Trp Tyr
225                 230                 235                 240
Thr Ser Asp Trp Val Arg His Gln Arg Asn Glu Ala Asp Gln Asp Leu
                245                 250                 255
Phe Val Val Gly Glu Tyr Trp Lys Asp Asp Val Gly Ala Leu Glu Phe
                260                 265                 270
Tyr Leu Asp Glu Met Asn Trp Glu Met Ser Leu Phe Asp Val Pro Leu
                275                 280                 285
Asn Tyr Asn Phe Tyr Arg Ala Ser Gln Gln Gly Gly Ser Tyr Asp Met
        290                 295                 300
Arg Asn Ile Leu Arg Gly Ser Leu Val Glu Ala His Pro Met His Ala
305                 310                 315                 320
Val Thr Phe Val Asp Asn His Asp Thr Gln Pro Gly Glu Ser Leu Glu
                325                 330                 335
Ser Trp Val Ala Asp Trp Phe Lys Pro Leu Ala Tyr Ala Thr Ile Leu
                340                 345                 350
Thr Arg Glu Gly Gly Tyr Pro Asn Val Phe Tyr Gly Asp Tyr Tyr Gly
        355                 360                 365
Ile Pro Asn Asp Asn Ile Ser Ala Lys Lys Asp Met Ile Asp Glu Leu
        370                 375                 380
Leu Asp Ala Arg Gln Asn Tyr Ala Tyr Gly Thr Gln His Asp Tyr Phe
385                 390                 395                 400
Asp His Trp Asp Val Val Gly Trp Thr Arg Glu Gly Ser Ser Ser Arg
                405                 410                 415
Pro Asn Ser Gly Leu Ala Thr Ile Met Ser Asn Gly Pro Gly Gly Ser
                420                 425                 430
Lys Trp Met Tyr Val Gly Arg Gln Asn Ala Gly Gln Thr Trp Thr Asp
        435                 440                 445
Leu Thr Gly Asn Asn Gly Ala Ser Val Thr Ile Asn Gly Asp Gly Trp
        450                 455                 460
Gly Glu Phe Phe Thr Asn Gly Gly Ser Val Ser Val Tyr Val Asn Gln
465                 470                 475                 480
```